United States Patent [19]

Kobayashi et al.

[11] Patent Number: 5,866,374
[45] Date of Patent: Feb. 2, 1999

[54] GENE CONFERRING FLOCCULATING PROPERTY ON YEAST AND GENE PRODUCT THEREOF

[75] Inventors: Osamu Kobayashi; Nobuyuki Hayashi; Hidetaka Sone, all of Kanagawa, Japan

[73] Assignee: Kirin Beer Kabushiki Kaisha, Tokyo, Japan

[21] Appl. No.: 716,284

[22] PCT Filed: Jan. 31, 1996

[86] PCT No.: PCT/JP96/00183

§ 371 Date: Oct. 1, 1996

§ 102(e) Date: Oct. 1, 1996

[87] PCT Pub. No.: WO96/23877

PCT Pub. Date: Aug. 8, 1996

[30] Foreign Application Priority Data

Feb. 1, 1995 [JP] Japan ..................................... 7-015449
May 2, 1995 [JP] Japan ..................................... 7-108688

[51] Int. Cl.[6] .......................... C12N 15/31; C12N 15/81; C07K 7/00; C07K 14/395
[52] U.S. Cl. .......................... 435/69.9; 435/41; 435/69.1; 435/172.3; 435/254.21; 435/320.1; 536/23.1; 536/23.7; 530/300; 530/324; 530/327; 530/350
[58] Field of Search .................................. 536/23.1, 23.7; 435/254.21, 71.1, 41, 69.9, 69.1, 161; 530/350, 300, 324, 327

[56] References Cited

FOREIGN PATENT DOCUMENTS

WO 94/19475  9/1994  WIPO.

OTHER PUBLICATIONS

Teunissen et al., Sequence of the Open Reading Frame of the FLO1 Gene From Saccharomyces Cerevisiae, Yeast, (1993), V. 9, pp. 423–427.

Watari et al., Construction of Flocculent Brewers's Yeast by Chromosomal Integration of the Yeast Flocculation Gene FLO1, J. Inst. Brew., (1994), V. 100, pp. 73–77.

Teunissen et al., The Dominant Flocculation Genes of Saccharomyces Cerervisiae Constitute a New Subtelomeric Gene Family, Yeast, (1995), V. 11, pp. 1001–1013.

Murakami, Analysis of the Nucleotide Sequence of Chromosome VI From Saccharomyces Cerevisiae, Nature Genetics, (1995), V. 10, pp. 261–268.

Yamashita, Mating Signals Control Expression of Both Starch Fermentation Genes and a Novel Flocculation Gene FLO8 in the Yeast Saccharomyces, Agric. Biol. Chem., (1983), V. 47 (12), pp. 2889–2896.

Stewart, Biochemical and Genetic Studies on Yeast Flocculation, Kem.–Kemi, (1976), V. 3 (10), pp. 465–479.

Russell, Spheroplast Fusion of Brewer's Yeast Strains, J. Inst. Brew., (1979), V. 85, pp. 95–98.

Watari, Breeding of Flocculent Industrial Saccharomyces Cerevisiae Strains by Introducing the Flocculation Gene FLO1, Agric. Biol. Chem., (1991), vol. 55 (6), pp. 1547–1552.

Watari, Molecular Cloning and Analysis of the Yeast Flocculation Gene FLO1, Yeast, (1994), V. 10, pp. 211–225.

Bidard, Cloning and Analysis of a FLO5 Flocculation Gene From S. Cerevisiae, Curr Genet, (1994), V. 25, pp. 196–201.

Sieiro, Flocculation of Industrial and Laboratory Strains of Saccharomyces Cerevisiae, J. Industrial Microbiology, (1995), V. 14, pp. 461–466.

Teunissen, Transcriptional Regulation of Flocculation Genes in Saccharomyces Cerevisiae, Yeast, (1995), V. 11, pp. 435–446.

By Brewing Society of Japan "Journal by Brewing Society of Japan", Sep. 15, 1993, Brewing Society of Japan, pp. 665–670.

Stewart, Can a Genetically Manipulated Yeast Strain Produce Palatable Beer?, J. Am. Soc. Brew. Chem., (1977), V. 35 (4), pp. 168–178.

Barney, Use of Genetic Transformation for the Introduction of Flocculence Into Yeast, J. Am. Soc. Brew. Chem., (1980), V. 38(2) pp. 71–74.

*Primary Examiner*—John L. LeGuyader
*Assistant Examiner*—Mark L. Shibuya
*Attorney, Agent, or Firm*—Foley & Lardner

[57] ABSTRACT

A protein designated "Lg-Flo1" can be produced recombinantly and confers brewer's yeast-type flocculating property, for example, when Lg-FLO1 DNA is expressed in non-flocculent yeast strain. Conversely, a flocculent yeast strain can be rendered non-flocculent by eliminating or disrupting the ability of the strain to express Lg-Flo1.

21 Claims, 9 Drawing Sheets

Results of Southern and Northern Analyses on *FLO1* Gene in Brewer's Yeast Strain and Meiotic Segregants Thereof Restriction Map of Lg-*FLO1* Gene Abbreviations represent the following restriction sites: Bm: BamHI, Ec:EcoRI, Hd:HindIII, Kp:KpnI, Pt:PstI, Sa:SalI, Xb:XbaI, Xh:XhoI.

Due to the nature of the experiment, only those restriction sites located closest to the annealing site of FLO1 probe are shown. Other sites, even if they exist, are not shown.

FIG.3

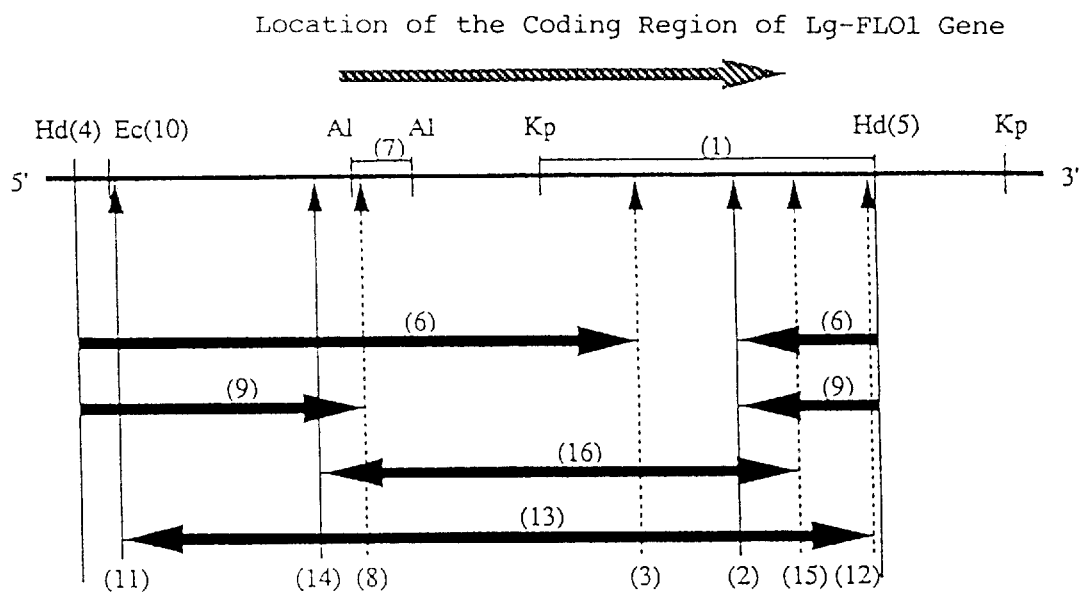

Concept Diagram of Cloning of the Full Length of Lg-*FLO1* by Inverse PCR

For figures in parentheses, see explanation given in the specification. Upward arrows indicate positions of primers. (Solid lines represent 5'→3' primers and dotted lines 3'→5' primers.) Bold, solid arrows represent PCR fragments. Abbreviations represent the following restriction enzymes: Hd: HindIII, Ec:EcoRI, Al:AluI and Kp:KpnI.

Restriction Map of Lg-*FLO1* Full Length Fragment
Abbreviations represent the following restriction sites: Bm: BamHI, Pt:PstI, Sl:SalI, Sp:SpeI, Sh:SphI, Xb:XbaI.
The SalI site has been given by primers and is not present in the chromosome.

Concept Diagram of Construction of Lg-Sc-Chimeric FLO1 Gene

Construction of a Plasmid for Lg-FL01 Disruption

Construction of a Plasmid for Lg-FLO1 Disruption (continued)

FIG.8

```
             10         20         30         40         50         60
Lg-FLO1  MTIAHHCIFLVILAFLELLNVASGSTQACLPVGSRKNGMNVNFYKYSLQDSTTYSDPQYM
         X:...:...::.....:.: .::::..:.::::.: ::.:::.:::.:::.::.::...::
Sc-FLO1  MTMPHRYMFLAVFTLLALTSVASGATEACLPAGQRKSGMNINFYQYSLKDSSTYSNAAYM 70         80         90        100        110        120
Lg-FLO1  AYKYSDTKKLGSVSGQTHLSIYY-----------------------GPNTAFWNTA
         :: :....:::::.:::..:: :                        :. ... ..:
Sc-FLO1  AYGYASKTKLGSVGGQTDISIDYNIPCVSSSGTFPCPQEDSYGNWGCKGMGACSNSQGIA 130        140        150        160        170        180
Lg-FLO1  SWSSDLFGFYTTPTNVTVEMTGYFLPPQTGSYTFKFATVDDSAILSVGGSIAFECCAQEQ
         ::.:::::::::::::.:::::::::::::::::::::::::::::::..::.:::::.:
Sc-FLO1  YWSTDLFGFYTTPTNVTLEMTGYFLPPQTGSYTFKFATVDDSAILSVGGATAFNCCAQQQ 190        200        210        220        230        240
Lg-FLO1  PPITSTDFTINGIKPWDAAAPTDIKGSTYMYAGYYYPIKIVYSNAKVLARLPVSVVLPDG
         ::::::.:::.::::::...  :...:..:::::::::.::::::    . ::.::.:::X
Sc-FLO1  PPITSTNFTIDGIKPWGGSLPPNIEGTVYMYAGYYYPMKVVYSNAVSWGTLPISVTLPDG
```

Comparison of Deduced Amino Acid Sequences
for N-Terminal Regions of Lg-*FLO1* and Sc-*FLO1*

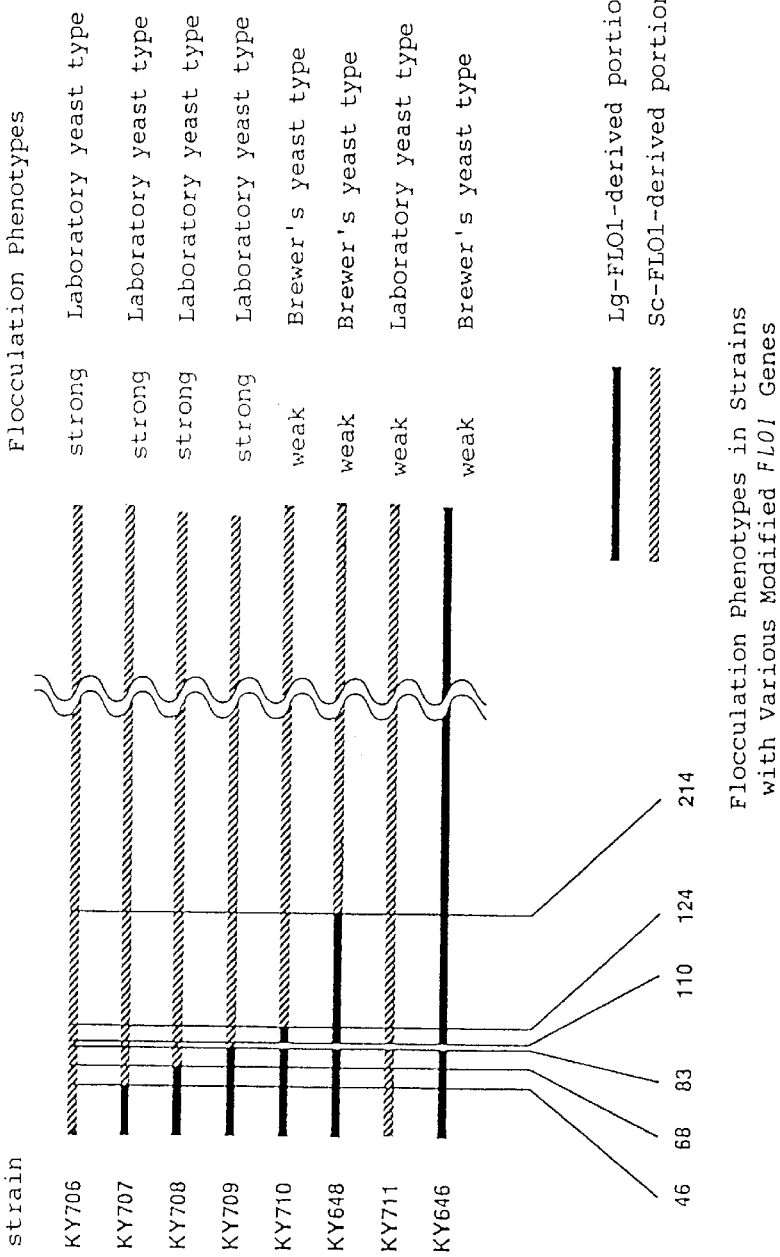

FIG. 9

Flocculation Phenotypes in Strains with Various Modified FLO1 Genes

Various modified FLO1 Genes were ligated in the downstream of the GAL1 gene and introduced into FLO1-disrupted laboratory yeast. Then, flocculating property was evaluated. In flocculation phenotypes, "strong" represents the extent of flocculation as seen in laboratory yeast and "weak" the extent of flocculation as seen in brewer's yeast. With respect to inhibition by sugars, flocculation inhibited by mannose but not inhibited by glucose is expressed as "laboratory yeast type" and flocculation inhibited by either mannose or glucose is expressed as "brewer's yeast type". The figures given at the bottom line indicate the amino acid numbers counted from the N-terminal. When compared to Sc-FLO1, Lg-FLO1 has a deletion of amino acids from position 84 to position 110, but the above amino acid numbers counted from the N-terminal have been converted to the numbers based on Sc-FLO1.

GENE CONFERRING FLOCCULATING PROPERTY ON YEAST AND GENE PRODUCT THEREOF

This is the U.S. national stage, filed under 35 U.S.C. 371, of PCT/JP96/00183 filed Jan. 31, 1996.

1. Field of the Invention

The present invention relates to a yeast flocculation gene and the use thereof. More specifically, the present invention relates to a protein having an activity of conferring on yeast brewer's yeast-type flocculating property, a DNA coding for the protein, a plasmid containing the DNA, a method for producing a yeast strain wherein brewer's yeast-type flocculating property has been conferred or enhanced with the use of the DNA, a method for producing a yeast strain wherein brewer's yeast-type flocculating property has been eliminated or reduced with the use of the DNA, and a method for eliminating or reducing brewer's yeast-type flocculating property of yeast by inhibiting the expression of the DNA.

The present invention also relates to a yeast strain wherein brewer's yeast-type flocculating property has been conferred, enhanced, eliminated or reduced by one of the above-mentioned methods.

Further, the present invention relates to a method for producing brewed products comprising culturing the above yeast strain as well as brewed products obtained by the method.

2. Background Art

It is a well known fact that, in alcoholic drinks such as beer and wine, the flocculating property of yeast used in fermentation is important not only because it determines the flavor and taste of the resultant products but also because it influences the workability in the fermentation process. The yeast which is used in the brewing of lager beer widely produced in Germany, Japan and many other countries has a characteristic that cells flocculate and sediment to the bottom of the fermented wort near the end of fermentation; such yeast is particularly called bottom fermenting yeast. In beer brewing, there is a characteristic feature in the process not found in other brewing, that is, yeast cells sedimented at the end of fermentation are recovered and reused in the subsequent fermentation. Accordingly, the characteristic of bottom fermenting yeast that it sediments at the late stage of fermentation has an especially big meaning for beer brewing.

Since brewer's yeast is one of the major factors that determine the quality of the final beer product, the breeding of excellent yeast strains is an important subject for beer brewers. In the breeding of bottom fermenting yeast, the conferring of a suitable flocculating property on yeast has a significant meaning. This is because a yeast strain too strong in flocculating property precipitates in the fermented wort during the fermentation, which leads to the termination of the fermentation, and, on the other hand, a yeast strain lacking flocculating property remains suspending even at the late stage of the fermentation and an operation such as centrifugation is needed to remove yeast cells from fermented wort. Therefore, a desirable yeast strain for the current production method is a strain which is dispersed at the beginning of the fermentation and precipitates well at the late stage of the fermentation. If the production method is different, needless to say, a yeast strain having a flocculating property suitable for the method is required.

In spite of the numerous studies concerning the yeast flocculating property which is industrially significant, the mechanism of yeast flocculation has not been elucidated yet. It is hard to say that control of flocculating property by improving a yeast strain per se is successful. As a result of years of genetic researches, the existence of yeast genes such as FLO1, flo3, FLO5, FLO8, sfl1, fsu1, fsu2, tup1, cyc8, cka2, FMC1 as well as the genes oli1 and oxi2 in mitochondrial DNA have been confirmed as genes involved in the flocculating property of yeast. As a study of these genes involved in the flocculating property of yeast at the molecular level, the isolation and analysis of the FLO1 gene has been performed [Yeast, 9, 423 (1993) and Yeast, 10, 211 (1994)]. Also, the isolation and analysis of the FLO5 gene has been reported. This report has shown that, although the location of the FLO5 gene is different from that of the previously reported FLO1 gene in the yeast chromosomal DNA, the restriction map and nucleotide sequence of FLO5 gene are almost identical with those of FLO1 [J. Inst. Brew., 85, 95, (1979) and Curr. Genet., 25, 196 (1994)].

However, the analysis of these genes at the molecular level have not been sufficient and it has not been elucidated yet in what mechanism these genes are involved in the flocculating property of yeast. Furthermore, with respect to genes other than FLO1 and FLO5 involved in the yeast flocculating property, even isolation or structural analysis has not been performed. No report has been made on the proteins which these genes code for.

As an attempt to improve the flocculating property of yeast by using such a gene as described above involved in that property, there has been a report in which flocculating property was conferred on various non-flocculent yeast strains including brewer's yeast by introducing the FLO1 gene, a flocculation gene of Saccharomyces cerevisiae [Agric. Biol. Chem., 55, 1547 (1991)]. However, it has been reported that the flocculating ability of the thus obtained transformed brewer's yeast is expressed from the initial stage of fermentation and that fermentation tends to be delayed [Journal of the Brewing Society of Japan, 88, 665 (1993)]. Thus, the conferring of flocculating property on yeast with this FLO1 gene cannot be said to be controlled in a favorable mode, and further improvement has been required in order to put such a method into actual use. Furthermore, although FLO1 gene has been known to be able to confer on yeast flocculating property, the role of its gene product in yeast flocculation has not been elucidated. As a result of the analysis of the amino acid sequence deduced from the nucleotide sequence for FLO1 gene, it has been presumed that the FLO1 gene product is localized in the surface layer of yeast cells. It seems that this presumption is also supported by a report that the amino acid sequence of the N-terminal 14 residues of a protein (flocculin) obtainable specifically from the surface layer of flocculent brewer's yeast cells has some homology to the amino acid sequence presumed from the nucleotide sequence for FLO1 gene [Appl. Environ. Microbial., 60, 2754 (1994)], but the mechanism of the above protein has not been elucidated yet. Consequently, the attempt to control yeast flocculation by the FLO1 gene has reached its limits.

As an attempt to use a gene other than FLO1, the conferring of a hereditary character on yeast was tried using the FLO5 gene and the cell fusion method, and the utility of conferring of the hereditary character has been shown [J. Inst. Brew., 98, 315 (1992)]. However, since the method of introducing a hereditary character is the cell fusion method, it was difficult to obtain a yeast strain having the character of interest and, furthermore, there has arisen a problem that DNA sequences other than the flocculation-related gene of interest are introduced into the resultant yeast strain; e.g., the POF1 gene which adds the phenolic flavor to beer and which many strains of *Saccharomyces cerevisiae* have is introduced simultaneously [Proc. Eur. Brew. Conv. 497 (1981)]. Thus, the improvement of flocculating property of useful yeast strains by this method cannot be said to be controlled.

As so far described, the improvements of the flocculation ability of yeast using those genes involved in yeast flocculation which have been attempted to date are of no practical use.

Under circumstances, the present invention aims at the following matters:

(1) to provide a protein having an activity of conferring on yeast brewer's yeast-type flocculating property:
(2) to provide a DNA strand coding for a protein having an activity of conferring on yeast brewer's yeast-type flocculating property:
(3) to provide a method for producing a yeast strain wherein brewer's yeast-type flocculating property has been conferred or enhanced with the use of the above DNA strand, or a method for producing a yeast strain wherein brewer's yeast-type flocculating property has been eliminated or reduced with the use of the above DNA strand, and a yeast strain wherein brewer's yeast-type flocculating property has been conferred, enhanced, eliminated or reduced by the above-mentioned method;
(4) to provide a method for eliminating or reducing brewer's yeast-type flocculating property of a yeast strain by inhibiting the expression of the above DNA strand; and
(5) to provide also a method for producing brewed products comprising culturing the yeast strain described above as well as brewed products obtained by the method.

DISCLOSURE OF THE INVENTION

Toward the solution of the problems described above, the present inventors have made intensive and extensive researches into the flocculating property of bottom fermenting brewer's yeast. As a result, the inventors confirmed the existence of the FLO1-homologous gene which flocculent bottom fermenting yeast specifically has (hereinafter referred to as the "Lg-FLO1 (gene)"), and elucidated the relationship between the Lg-FLO1 gene and flocculating property. Subsequently, the inventors allowed the LG-FLO1 gene product to be produced in a yeast strain which had become non-flocculent due to the disraption of FLO1 caused by the introduction of Lg-FLO1. As a result, the inventors have found that brewer's yeast-type flocculation can be induced by the introduction of Lg-FLO1 gene. This finding implies not only the conferring of brewer's yeast-type flocculating property but also the conversion of a yeast strain having an laboratory yeast-type flocculating property into a yeast strain having brewer's yeast-type flocculating property. Further, the inventors have determined the region of the Lg-FLO1 gene product which controls the brewer's yeast-type flocculation in yeast. Also, the inventors have succeeded in converting a flocculent, brewer's yeast strain into a non-flocculent strain by introducing thereinto a disrupted Lg-FLO1 gene. Thus, the present invention has been achieved.

The present invention provides the Lg-FLO1 gene product having the amino acid sequence shown substantially in SEQ ID NO: 2 in the Sequence Listing; or a protein which comprises a peptide having the amino acid sequence shown substantially in SEQ ID NO: 2 in the Sequence Listing and which has an activity of conferring on yeast brewer's yeast-type flocculating property: or a protein which comprises a polypeptide having a partial sequence of the amino acid sequence shown substantially in SEQ ID NO: 2 in the Sequence Listing containing the amino acid residues from position 25 to position 213 and which has an activity of conferring on yeast brewer's yeast-type flocculating property: or a protein which comprises a polypeptide having a partial sequence of the amino acid sequence shown substantially in SEQ ID NO: 2 in the Sequence Listing containing at least the amino acid residues from position 25 to position 97 and which has an activity of conferring on yeast brewer's yeast-type flocculating property: and a polypeptide which has an activity of conferring on yeast brewer's yeast-type flocculating property and which has the amino acid sequence shown substantially in SEQ ID NO: 4 in the Sequence Listing. The term "substantially" used herein means that the amino acid sequence may have deletion, substitution, addition, polymerization and the like of one or several amino acid residues as long as the amino acid sequence has an activity of conferring on yeast brewer's yeast-type flocculating property.

Also, the present invention provides a DNA strand comprising a nucleotide sequence coding for the amino acid sequence shown substantially in SEQ ID NO: 2 in the Sequence Listing, or a DNA comprising a nucleotide sequence coding for a polypeptide having a partial sequence of the amino acid sequence shown substantially in SEQ ID NO: 2 in the Sequence Listing containing the amino acid residues from position 25 to position 213; or a DNA comprising a nucleotide sequence coding for a polypeptide having a partial sequence of the amino acid sequence shown substantially in SEQ ID NO: 2 in the Sequence Listing containing at least the amino acid residues from position 25 to position 97. The term "substantially" used herein means that the amino acid sequence may have deletion, substitution, addition, polymerization and the like of one or several amino acid residues as long as the amino acid sequence has an activity of conferring on yeast brewer's yeast-type flocculating property.

Further, the present invention provides a DNA which comprises a nucleotide sequence coding for an amino acid sequence having an activity of conferring on yeast brewer's yeast-type flocculating property and which comprises a partial sequence of the nucleotide sequence shown in SEQ ID NO: 1 in the Sequence Listing containing the nucleotide sequence from position 59 to position 697 or a DNA complementary thereto; a DNA which comprises a nucleotide sequence coding for a protein having an activity of conferring on yeast brewer's yeast-type flocculating property and which comprises a partial sequence of the nucleotide sequence shown in SEQ ID NO: 1 in the Sequence Listing containing the nucleotide sequence from position 131 to position 697 or a DNA complementary thereto; a DNA comprising a partial sequence of the nucleotide sequence shown in SEQ ID NO: 1 in the Sequence Listing containing the nucleotide sequence from position 131 to position 349 or a DNA complementary thereto; and a DNA which comprises the nucleotide sequence shown in SEQ ID NO: 3 in the Sequence Listing and which codes for a polypeptide having an activity of conferring on yeast brewer's yeast-type flocculating property or a DNA complementary thereto.

The present invention also provides a DNA which is incorporated into plasmid KTYT2, YESKT2, KNWtC3 or KNYES and which comprises a nucleotide sequence coding for a protein having an activity of conferring on yeast brewer's yeast-type flocculating property as well as a plasmid comprising the above DNA.

Further, the present invention provides a method for producing a yeast strain wherein brewer's yeast-type flocculating property has been conferred or enhanced, characterized by introducing thereinto the above-mentioned DNA. The invention also provides a method for producing a yeast strain wherein brewer's yeast-type flocculating property has been eliminated or reduced, characterized by introducing thereinto a DNA of which the ability to express a protein having an activity of conferring brewer's yeast-type flocculating property has been eliminated or reduced by disrupting the above-mentioned DNA.

Still further, the present invention provides a yeast strain which is produced by any one of the above-mentioned methods and in which brewer's yeast-type flocculating property has been conferred, enhanced, eliminated or reduced.

The present invention also provides a method for eliminating or reducing brewer's yeast-type flocculating property of yeast by inhibiting the expression of the above-mentioned DNA.

Further, the present invention provides a method for producing brewed products comprising culturing the yeast strain described above as well as brewed products obtained by the method.

BRIEF DESCRIPTION OF THE DRAWINGS

FIG. 3 shows a concept diagram of the full length cloning of the LG-FLO1 gene by inverse PCR.

FIG. 8 shows comparison of the deduced amino acid sequences for N-terminal portions of the Lg-FLO1 gene (SEQ ID NOS: 2 and 19) and the Sc-FLO1 gene, respectively.

FIG. 9 shows the phenotypes of flocculation in those strains having various modified FLO1 genes.

BEST MODE FOR CARRYING OUT THE INVENTION

Figure 1:
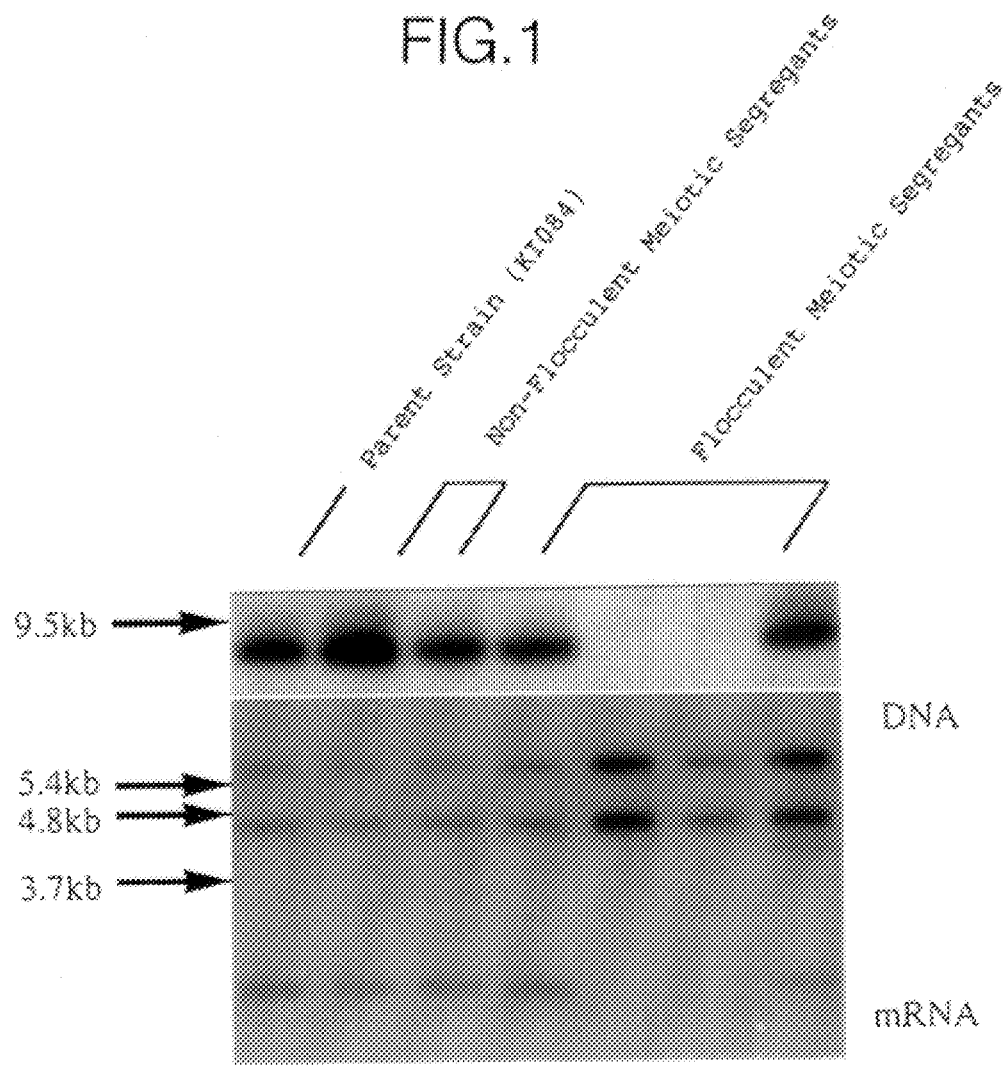
FIG. 1 shows the results (photographs) of electrophoresis in Southern and Northern analyses of a brewer's yeast strain and meiotic segregants thereof.

Hereinbelow, the present invention will be described in detail.

It should be noted that the terms "DNA", "nucleotide sequence", "gene" and "DNA strand" are used herein as having substantially the same meaning. Also, it should be noted that the terms "amino acid sequence", "peptide" and "protein" are used herein as having substantially the same meaning.

<Intercellular Flocculation in Yeast>

It is known that intercellular flocculation in yeast is attributable to sexual flocculation between a cells and α cells, unseparatedness of budding daughter cells from mother cells, non-sexual flocculation and so forth. Of these factors, the present invention aims at controlling non-sexual flocculation.

As a model for explaining the mechanism of non-sexual flocculation, the lectin hypothesis is strong that two neighboring yeast cells make interaction to each other through the linkage of a lectin like protein in the surface layer of flocculent yeast cells with sugar chains [J. Bacteriol., 150, 878 (1982)], but the lectin like protein has not been identified yet. This is one of the reasons for which the control of yeast flocculation is still difficult.

It has been reported that non-sexual flocculation can be roughly classified into two types depending on the kind of sugar which inhibits the flocculation, i.e., mannose-specific Flo1 type flocculation and NewFlo type flocculation which is inhibited by maltose, glucose and the like in addition to mannose [Yeast, 7, 559 (1991)]. The present inventors have found that the flocculating property of common bottom fermenting yeast is classified into the NewFlo type. For facilitating understanding, these types of flocculation properties are expressed with the following terms.

Briefly, the flocculating property of common laboratory yeasts that is inhibited by co-existing mannose but not inhibited by maltose and glucose is expressed herein with the term "laboratory yeast-type flocculating property". On the other hand, the flocculating property of those yeasts strains represented by common bottom fermenting brewer's yeast that is inhibited by maltose, glucose and the like in addition to co-existing mannose is expressed with the term "brewer's yeast-type flocculating property". Both types of flocculating properties are not inhibited by galactose. The present inventors presume it very important, at least in beer brewing, that bottom fermenting brewer's yeast has the "brewer's yeast-type flocculating property" for the reasons described below. Briefly, this "brewer's yeast-type flocculating property" is greatly different from the flocculating property of laboratory yeast in that the former is inhibited by glucose, maltose and the like. Beer is produced by brewing wort with brewer's yeast. Since about 6% of maltose and about 1% of glucose are contained in wort, the fact that the flocculation of brewer's yeast is inhibited by these sugars has an important meaning. In other words, it can be conjectured as follows. Due to the characteristic of the "brewer's yeast-type flocculating property", brewer's yeast added to wort is prevented from flocculation by sugars contained therein and able to disperse into the wort. Thus, the fermentation proceeds rapidly, and when sugar concentrations in the fermented wort decrease at the late stage of the fermentation, inhibition of flocculation becomes weakened. As a result, yeast cells form flocs and sediment to thereby make it easy to recover them.

<Lg-Flo1 Protein>

Lg-Flo1 protein is the protein encoded by the FLO1-homologous gene, namely the Lg-FLO1 gene, peculiar to bottom fermenting brewer's yeasts and meiotic segregants thereof exhibiting the brewer's yeast-type flocculating property.

The present invention includes the Lg-Flo1 protein and derivatives thereof. The Lg-Flo1 protein may be derived from yeast, in particular *Saccharomyces cerevisiae* and it has a characteristic of being capable of conferring on yeast the brewer's yeast-type flocculating property. The Lg-Flo1 protein contains in its amino acid sequence the amino acid sequence shown substantially in SEQ ID NO: 2 in the Sequence Listing. "The amino acid sequence shown substantially in SEQ ID NO: 2 in the Sequence Listing" includes, in addition to "the amino acid sequence shown in SEQ ID NO: 2 in the Sequence Listing", the amino acid sequence of SEQ ID NO: 2 having modifications, i.e., having addition, insertion, deletion or substitution of one or more amino acid residues, as long as the amino acid sequence confers on yeast the brewer's yeast-type flocculating property.

"The amino acid sequence shown in SEQ ID NO: 2 in the Sequence Listing" of the invention has some homology to the amino acid sequence deduced from the known nucleotide sequence for the laboratory yeast FLO1 gene. However, the decisive difference between the two is that the Lg-Flo1 protein and derivatives thereof comprising "the amino acid sequence shown in SEQ ID NO: 2 in the Sequence Listing" of the invention can confer on yeast the "brewer's yeast-type flocculating property" described above which is an important characteristic for brewer's yeast. Upon completion of the present invention, it has been shown for the first time that the Lg-Flo1 protein and derivatives thereof can confer on yeast the "brewer's yeast-type flocculating property".

With respect to flocculin which is a protein obtained from the surface layer of flocculent brewer's yeast cells, its biological functions have not been elucidated yet but the amino acid sequence for the 16 residues at its N-terminal has been determined (SEQ ID NO: 5)*TQACLPVG*RKNGMN: * represents an unidentified amino acid residue) [Appl. Environ. Microbiol., 60, 2754 (1994)]. The Lg-Flo1 protein of which the functions have been elucidated by the present invention for the first time comprises this amino acid sequence (from position 25 to position 40 of SEQ ID NO: 2 in the Sequence Listing). At present, there is no evidence showing that the Lg-Flo1 protein of the invention is identical with flocculin. However, in the Lg-Flo1 protein of the invention also, there is an extremely high possibility that the region represented by the amino acid sequence extending from position 1 to position 24 of SEQ ID NO: 2 is a secretion signal sequence necessary for the Lg-Flo1 protein to be localized in the surface layer of cells. Accordingly, it is conjectured that the protein which is localized in the surface layer of flocculent yeast cells and which has an activity of conferring on yeast flocculating property is a protein having the amino acid sequence covering from position 25 to the end of SEQ ID NO: 2 in the Sequence Listing.

<Lg-FLO1 gene>

The present invention includes the DNA strand of Lg-FLO1. The term "the DNA strand of Lg-FLO1" used herein denotes a DNA comprising a nucleotide sequence coding for the Lg-Flo1 protein or a derivative thereof having an activity of conferring on yeast the brewer's yeast-type flocculating property.

More specifically, the present invention includes a DNA strand comprising a nucleotide sequence coding for a protein having the amino acid sequence shown substantially in SEQ ID NO: 2 in the Sequence Listing. Here, it should be noted that the expression "a nucleotide sequence coding for a protein having the amino acid sequence" means all the different nucleotide sequences which may be generated due to degeneracy of genetic codes.

What was indispensable for the completion of the present invention was the finding described in Example 1 that a bottom fermenting yeast strain and meiotic segregants thereof exhibiting the brewer's yeast-type flocculating property have the distinctive FLO1-homologous gene. In the present specification, this "FLO1-homologous gene distinctive of bottom fermenting yeast and meiotic segregants thereof exhibiting the brewer's yeast-type flocculating property" is expressed with the term "the Lg-FLO1 gene". However, the above finding alone could not at all have lead to the fact that "the Lg-FLO1 gene" has an activity to render on yeast the "brewer's yeast-type flocculating property". Further elaboration was required for the completion of the present invention.

From another point of view, the present invention also includes a DNA which is incorporated in plasmid KTYT2 and which comprises a nucleotide sequence coding for a protein having an activity to render on yeast the brewer's yeast-type flocculating property.

Hereinafter, the DNA's of the present invention as described above are collectively called "the LG-FLO1 DNA" strand.

The Lg-FLO1 DNA strand of the invention may be a naturally occurring DNA, a totally synthesized DNA, or a partially synthesized DNA which has been synthesized using a part of a naturally occurring DNA.

<Transformation>

By introducing the Lg-FLO1 gene DNA strand of the invention, it is possible to obtain a yeast strain wherein the brewer's yeast-type flocculating property has been conferred or enhanced.

As a method for introducing the Lg-FLO1 DNA strand, standard techniques conventionally used in the field of genetic engineering may be used in accordance with conventional standards [see, e.g., Analytical Biochemistry 163, 391 (1987)]. Specific examples of such methods include, e.g., a method in which a desired DNA is incorporated into a vector, that is then introduced into yeast cells and a method in which a desired DNA is directly introduced into yeast cells without incorporation into a vector.

In the former method in which a desired DNA is incorporated into a vector, that is then introduced into yeast cells, vectors which may be used for this purpose include, for example, a YRp vector (a yeast multicopy vector using an ARS sequence of the yeast chromosome as its replication origin), a YEp vector (a yeast multicopy vector having a replication origin of yeast 2 $\mu$m DNA), a YCp vector (a yeast single copy vector having an ARS sequence of the yeast chromosome as its replication origin and also having a centromere sequence of the yeast chromosome) and a YIp vector (a vector to be integrated into the yeast chromosome, not having a replication origin of yeast); any of known vectors may be used. These vectors are disclosed in literature (see "New Biotechnology of Yeast", Medical Publication Center, p. 284) and may be readily prepared.

As a representative technique of introducing DNA directly into yeast cells without the incorporation of the DNA into a vector, the co-transformation method may be given in which yeast cells are co-transformed with a plasmid having a marker gene (such as a drug resistance gene) and a DNA sequence to be introduced (Japanese Examined Patent Publication No. 5-60918).

In such methods as described above, in order to express the introduced DNA sequence in yeast or to enhance or reduce its expression, a promoter (which is a unit controlling transcription and translation) and a terminator are incorporated into the DNA chain of the invention in a 5' upstream region and a 3' downstream region, respectively. As a promoter and a terminator for the above purposes, those derived from known genes such as alcohol dehydrogenase gene [J. Biol. Chem., 257, 3018 (1982)], phosphoglycerate kinase gene [Nucleic Acids Res., 10, 7791 (1982)], glycerolaldehyde-3-phosphodehydrogenase gene [J. Biol. Chem., 254, 9839 (1979)], or those which have been obtained by artificially improving the above ones may be used in addition to those derived from the Lg-FLO1 gene per se. More specifically, promoters and terminators such as ADH (also known as ADC), GAPDH (also known as GPD), PHO, GAL, PGK, ENO, TRP and HIP may be used.

Further, by selecting an appropriate promoter, it is also possible to allow the gene having the DNA chain of the invention to be expressed in yeast cells in a controlled manner. For example, when a promoter from galactokinase gene is used, expression of the gene can be increased by changing the sugar source of a medium, for example, from glucose to galactose.

Furthermore, by introducing a DNA of which the ability to express the Lg-Flo1 protein has been eliminated or reduced by disrupting the LG-FLO1 gene, it is possible to obtain a yeast strain of which the flocculating property has been eliminated or reduced. The disruption of the Lg-FLO1 gene may be achieved by adding or deleting one or more bases in a region involved in the expression of the Lg-Flo1 protein in the Lg-FLO1 gene (such as the promoter region or the coding region), or by deleting such a region as a whole. A DNA of which the ability to express the Lg-Flo1 protein has been eliminated or reduced by disrupting the Lg-FLO1 gene may be introduced into yeast cells using the same technique as used in the above-mentioned DNA introduction. It is considered as follows. With the introduction of this DNA, homologous recombination occurs between the Lg-FLO1 gene in the chromosomal DNA of the host yeast cells and the introduced DNA, and the Lg-FLO1 gene of the host cells is interrupted. This leads to elimination or reduction of the ability to express the Lg-Flo1 protein, and, as a result, the flocculating property of the host yeast cells is eliminated or reduced.

A yeast strain to be transformed, i.e., a host yeast strain in the invention may be any which can be taxonomically classified into yeast. For the purpose of the invention, industrial yeast belonging to Saccharomyces cerevisiae, more specifically, brewer's yeast, wine yeast or yeast used for alcohol production is preferable.

The present invention also includes a method for eliminating or reducing the flocculating property of yeast by inhibiting the expression of the above-mentioned Lg-FLO1 gene. Specific examples of this method include a method of introducing a DNA of which the ability to express the Lg-Flo1 protein has been eliminated or reduced by disrupting the Lg-FLO1 gene, the antisense RNA method, and the like.

The present invention also includes a method, as described in (6) in Example 1, of converting the laboratory yeast-type flocculating property into the brewer's yeast-type flocculating property by substituting the above-mentioned Lg-FLO1 gene with the laboratory yeast-type FLO1 gene. Also, reverse conversion may be possible by using the Lg-FLO1 gene DNA provided by the invention.

Brewed products produced by a process comprising culturing the yeast strain of the invention include alcoholic drinks such as beer, Japanese sake, low-class distilled spirit, wine, whisky and brandy; seasonings such as soy sauce, miso and sweet sake; and fuel alcohols. As the method of the invention for producing brewed products, brewing processes relating to the above-mentioned brewed products are included.

Hereinbelow, the present invention will be described in more detail with reference to the following Examples, which should not be construed as limiting the scope of the invention.

[EXAMPLE 1]

Cloning of the FLO1 Homologous Gene Deeply Involved in Brewer's Yeast-Type Flocculation
(1) Search for Genes Involved in the Flocculating Property of Brewer's Yeast For the purpose of searching for genes involved in the flocculating property of brewer's yeast, the following experiment was carried out. From the flocculent brewer's yeast strain KI084, spores were allowed to form by the method of Stewart et al. [J. Inst. Brew., 93, 216–219, (1987)] to thereby prepare strains in which chromosome number was reduced (hereinafter, such strains are called "meiotic segregants"). Of the resultant meiotic segregants, 6 strains were cultured in the medium shown in Table 1 at 20° C. under static conditions for 48 hours. After cultivation, cells were harvested by centrifugation, washed with 0.1M EDTA twice and with sterilized water twice, and then resuspended in sterilized water. Judgment of the flocculating property of cells was carried out by the following method. Briefly, cells were suspended in flocculation measurement buffer (50 mM sodium acetate, 0.1% calcium chloride, pH 4.6) to give a final OD of OD600=2.0., left at room temperature for 30 minutes and then agitated vigorously for 20 seconds. Cells were left stationary for another 5 minutes, and then flocculation or non-flocculation was judged with the eye. As a result, the 6 meiotic segregant strains tested were grouped into 2 non-flocculent strains and 4 flocculent strains.

| Medium for Flocculation Measurement | |
|---|---|
| Galactose | 50 g/liter |
| YNB W/O AA & AS * | 1.7 g/liter |
| Amino acids | |
| Aspartic acid | 100 mg/l |
| Glutamic acid | 100 mg/l |
| Threonine | 100 mg/l |
| Serine | 100 mg/l |
| Lysine hydrochloride | 100 mg/l |
| Arginine | 100 mg/l |

* Yeast nitrogen base not containing amino acids nor ammonium sulfate.
In the culturing of transformants, the above medium supplemented with adenine sulfate, tryptophan and histidine hydrochloride each at a rate of 20 mg/l was used.

These strains were subjected to Southern analysis and Northern analysis as described blow. The extraction of total DNA was performed by culturing cells under shaking in YPD medium [2% bacto-peptone (Difco), 1% yeast extract (Difco), 2% glucose] at 30° C. and extracting the total DNA from those cells which reached stationary phase according to the method of Hereford et al [Cell, 18, 1261–1271, (1979)]. Two micrograms of the extracted DNA was digested with HindIII (Boehringer Mannheim) and subjected to electrophoresis using 1% agarose gel. Then, the DNA was blotted onto a nylon filter, Hybond N+ (Amersham), according to the protocol attached thereto and then subjected to the subsequent Southern analysis. On the other hand, the extraction of total RNA was performed on these strains by culturing them under static conditions in the medium shown in Table 1 at 20° C. for 48 hours and extracting the total RNA according to the method of Villeneve and Meyer [Cell, 48, 25–37 (1987)]. Ten micrograms of the thus obtained RNA was glyoxalized by treating in 16 $\mu$l of glyoxasl/DMSO solution [1M glyoxal, 50% DMSO, 10 mM sodium phosphate buffer (pH 7.0)] for 1 hour at 50° C. Thereafter, 2 $\mu$l of loading buffer [50% (w/v) glycerol, 10 mM phosphate buffer (pH 7.0), 0.4% (w/v) Bromophenol Blue] and 1 $\mu$l of 1 mg/ml ethidium bromide solution were added thereto, and the resultant solution was electrophoresed in a gel containing 10 mM sodium phosphate buffer (pH 7.0) and 1% agarose. During this electrophoresis, the buffer in the electrophoresis layer was constantly circulated by using a peristaltic pump to thereby avoid generation of pH gradient. When Bromophenol Blue reached about 70% of the length of the gel, electrophoresis was terminated. Then, RNA in the gel stained with ethidium bromide was observed using a UV transilluminator and it was confirmed that the RNA had not been degraded using ribosomal RNA as an indicator.

Thereafter, the RNA in the gel was blotted onto a nylon filter, Genescreen-Plus (DuPont), according to the protocol attached thereto, and this filter on which the RNA had been blotted was treated at 80° C. for 2 hours. Then, the filter was subjected to Northern analysis according to the protocol attached to Genscreen-Plus.

Partial length DNA fragments of the FLO1 gene which were used in Southern and Northern analyses as probes were prepared as follows. Based on the nucleotide sequence for the FLO1 gene reported by Teunissen et al. [Yeast, 9, 423–427 (1993)], two primers of 5'GATGAAACTGTCAT-TGTTGTCAAA3' and 5'TCGTTTCAGCAGCTAAAG-TAT3' (SEQ ID NOS: 6 and 7) were synthesized. With these primers, PCR was carried out using the total DNA of the flocculent strain ABXL-1D (a, FLO1, Yeast Genetic Stock Center) as a template, and the total PCR products were electrophoresed in 1% agarose gel. An amplified DNA fragment of 1045 bp (hereinafter referred to as the "FLO1 partial length fragment") was cut out from the gel and this fragment was recovered by using Prep-A-Gene (Bio-Rad). This fragment was labelled with [α-$^{32}$P] dCTP (Amersham) and used as a probe. The detection of radioactivity was carried out using an X-ray film.

The results are shown in FIG. 1. As a result of Southern analysis, there were detected in the parent strain KI084 four HindIII fragments of about 9.5 kb, 5.4 kb, 4.8 kb and 3.7 kb having homology to the FLO1 gene. Of these fragments, two fragments of about 4.8 kb and 3.7 kb were detected in all of the KI084-derived meiotic segregants tested. Further, only in four meiotic segregants which were judged flocculent in the flocculation judging test, a fragment of about 9.5 kb was also detected in addition to the common bands. Also, as a result of Northern analysis, the transcription product of the FLO1 gene was observed only in the parent strain and the four meiotic segregants which were judged flocculent in the flocculation judging test. From these results, it has been suggested that only the FLO1-homologous gene a part or the full length of which is contained in the HindIII fragment of about 9.5 kb among the three HindIII fragments homologous to the FLO1 gene is transcribed in KI084-derived meiotic segregants, and that only those strains which have this homologous gene exhibit flocculating property. Hereinafter, the FLO1-homologous gene a part or the full length of which is contained in the HindIII fragment of about 9.5 kb of the KI084 strain is designated as Lg-FLO1 (Lager Type-FLO1).

(2) Preparation of a Restriction Map of Lg-FLO1

Of KI084-derived meiotic segregants, one flocculent strain, KMS004, and one non-flocculent strain, KMS001, were selected. Their DNA's were prepared as described above and subjected to Southern analysis using several restriction enzymes independently or in combination of two enzymes and using as a probe the FLO1 partial length fragment described above. As a result, one band which was not observed in the non-flocculent meiotic segregant was always observed in the flocculent KMS004 strain in addition to two bands that were common with the non-flocculent meiotic segregant. It was considered that a part or the full length of Lg-FLO1 is contained in this band specific to the flocculent meiotic segregant. Thus, the length of this fragment was determined and a restriction map as shown in FIG. 2 was prepared.

(3) Cloning of a KpnI Fragment Containing a Partial Length of Lg-FLO1

Figure 2:
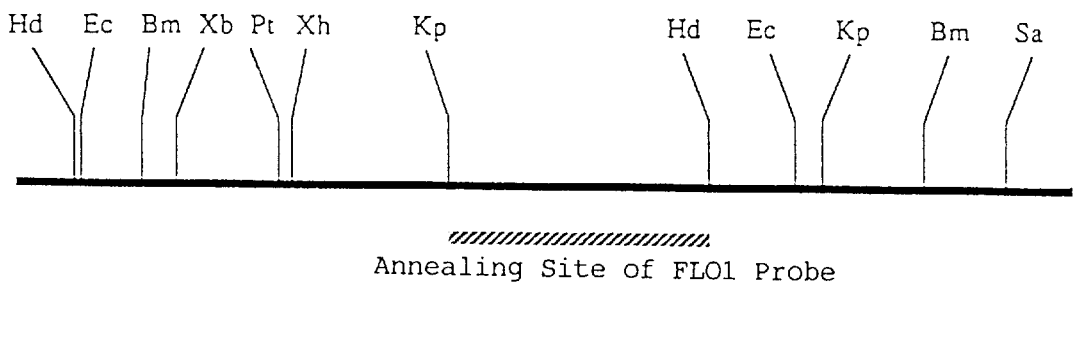
FIG. 2 shows a restriction map of the Lg-FLO1 gene.

Based on the restriction map shown in FIG. 2, the cloning of a KpnI fragment of about 5.6 kb was attempted. The DNA of the flocculent meiotic segregant KMS004 derived from KI084 was completely digested with KpnI (Boehringer Mannheim) and then fractionated by electrophoresis using 0.8% agarose. A mixture of DNA fragments of about 5.6 kb was cut out from the gel and purified by electroelution in a dialysis tube. As a result of Southern analysis using the above-mentioned FLO1 partial length fragment as a probe, it was confirmed that the DNA fragment of interest was contained in the purified DNA fragment mixture. Then, plasmid pUC18 (Takara Shuzo) completely digested with KpnI was ligated to the purified DNA fragment mixture using DNA Ligation Kit (Takara Shuzo), and then E. coli DH5$_\alpha$ (BRL) was transformed with the resultant plasmid. Of the resultant transformants obtained, 5000 strains were blotted on a nylon filter Hybond N+ (Amersham) according to the protocol attached to the filter, and colony hybridization was carried out using the above-mentioned FLO1 partial length fragment as a probe to thereby obtain 10 positive strains. Plasmids were prepared from these strains by the alkali method and analyzed with restriction enzymes. As a result, the plasmids contained in these strains were confirmed to have the same insertion fragment. The insertion fragment of plasmid pKF-Kpn11 from one of the above strains was subjected to Southern analysis using as control the DNA's of the flocculent meiotic segregant KMS004 and the non-flocculent meiotic segregant KMS001. As a result, it could be confirmed that the insertion fragment is a part of the Lg-FLO1 gene of interest.

(4) Partial Sequencing of the Nucleotide Sequence for a KpnI Fragment Containing a Partial Length of Lg-FLO1

In order to determine the nucleotide sequence for the insertion fragment from pKF-Kpn11, deletion series of the insertion fragment from pKF-Kpn11 were prepared using a deletion kit for kilosequence (Takara Shuzo) in accordance with the protocol attached to the kit. The nucleotide sequence was determined with a DNA sequencer (Perkin Elmer) using PCR/Sequencing Kit (Perkin Elmer). The nucleotide sequence was analyzed using DNASIS (Hitachi Software Engineering). The nucleotide sequence of 2.9 kb from KpnI site to HindIII site in which a coding region homologous to the coding region of known FLO1 had been found was determined from both directions. An ORF of 2.6 kb covering from the middle of the coding region of Lg-FLO1 to the termination codon was found in the determined nucleotide sequence.

(5) Acquisition of the Full Length of Lg-FLO1 by Inverse-PCR

The acquisition of the full length of Lg-FLO1 by inverse-PCR is shown typically in FIG. 3. From the previously determined nucleotide sequence for the partial length of Lg-FLO1 [(1) in FIG. 3], primer 5 [5'AATACACAACATGGTGTCCT3', (2) in FIG. 3] and primer8 [5'ACCAGAGGTGGAACTACTGG3', (3) in FIG. 3] were (SEQ ID NOS: 8 and 9) synthesized. DNA from the flocculent meiotic segregant strain KMS004 (60 µg) was digested with 300 units of HindIII (Boehringer Mannheim), recovered by ethanol precipitation and dissolved in 30 µgl of TE buffer. Self-ligation of the DNA fragments was carried out using DNA Ligation Kit (Takara Shuzo) in a scale of 300 µl. As a result, it is expected that cyclic molecules in which the HindIII sites represented by (4) and (5) in FIG. 3 were ligated are existing in the resultant reaction products. These reaction products were recovered by ethanol precipitation. Using 4 µg of these reaction products as a template and the above primer5 [(2) in FIG. 3] and primer8 [(3) in FIG. 3] as primers, an inverse-PCR was carried out with LA-PCR Kit (Takara Shuzo). The composition of the reaction solution was as recommended in the protocol attached to the kit. The reaction was conducted as follows using DNA Thermal Cycler 480 (Perkin Elmer): 1 cycle at 94° C. for 1 minute followed by 30 cycles at 98° C. for 20 seconds and at 68° C. for 10 minutes. As a result of the electrophoresis of the reaction products using 0.8% agarose, it was observed that DNA fragments of about 8.2 kb, about 3.6 kb and about 3.0 kb were amplified.

Of these DNA fragments, the fragment of about 8.2 kb [(6) in FIG. 3] was cut out from the gel and purified using Prep-A-Gene (Bio Rad) and according to the protocol attached thereto. Since this fragment contained the BamHI, EcoRI and XbaI sites indicated in the restriction map shown in FIG. 2, it was judged that a not-yet-obtained portion of Lg-FLO1 is contained in this fragment. This DNA fragment was digested with AluI (Boehringer Mannheim), ligated to the HincII site of pUC118 (Takara Shuzo) and introduced into E. coli DH5 strain (Toyobo). Plasmids were prepared from 30 strains of the resultant transformants, and the sizes of insertion fragments were examined. As a result, these plasmids could be classified into 24 groups. With respect to these plasmids, the nucleotide sequence for the insertion fragment was determined by the method as described above. As a result, one clone was obtained which has an insertion fragment of 467 bp highly homologous to the amino terminal portion of known FLO1. This plasmid was designated as KF1. The location of the insertion fragment of KF1 in the chromosome is represented by (7) in FIG. 3.

However, the insertion fragment of KF1 did not contain a sequence which appears to be a translation initiation site. Based on the nucleotide sequence for KF1, primerKN-2 [5'TTGTATCGGAGTATTTATA3', (8) in FIG. 3] (SEQ ID NO: 10) was synthesized. Subsequently, using the template used in the above inverse-PCR and using as primers the above primer5 [(2) in FIG. 3] and primerKN-2 [(8) in FIG. 3], inverse PCR was carried out with GeneAmp PCR Reagent Kit (Takara Shuzo). The composition of the reaction solution was as recommended in the protocol attached to the kit. The reaction was conducted as follows using DNA Thermal Cycler 480: 30 cycles at 94° C. for 1 minute, at 55° C. for 2 minutes and at 72° C. for 2 minutes followed by 1 cycle at 72° C. for 10 minutes. As a result of the electrophoresis of the reaction products using 0.8% agarose, it was observed that DNA fragments of about 4.4 kb, about 1.1 kb and about 0.6 kb were amplified. Of these fragments, the DNA fragment of about 4.4 kb [(9) in FIG. 3] was cut out from the gel, purified by the method described above, blunt-ended with Klenow fragment (Takara Shuzo), ligated to the HincII site of pUC118 and introduced into E. coli DH5 strain. KF14, which is a plasmid of one of the transformants obtained, contained the BamHI, EcoRI and XbaI sites indicated in the restriction map shown in FIG. 2. Therefore, it was judged that the translation initiation site of Lg-FLO1 and its 5' upstream region are contained in this fragment.

Figure 4:
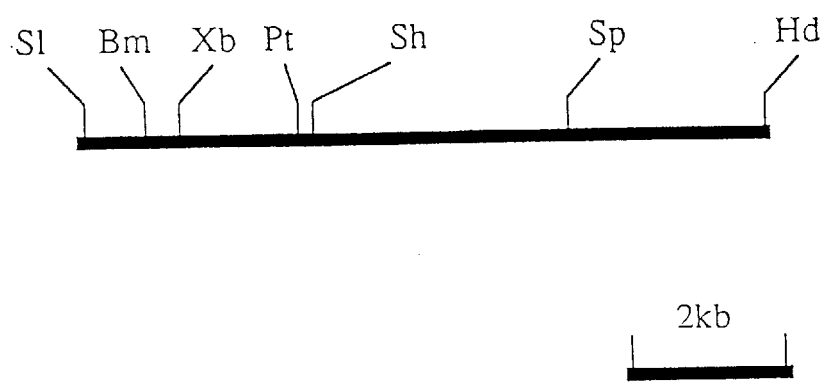
FIG. 4 shows a restriction map of the Lg-FLO1 gene full length fragment.

For the purpose of partially determining the nucleotide sequence for the insertion fragment of KF14 from the EcoRI site [represented by (10) in FIG. 3] toward 3', KF14 was digested with EcoRI and then a self-ligated plasmid, KF14ΔEc, was constructed. This plasmid has a fragment extending from the EcoRI site represented by (10) in FIG. 3 to the annealing site of primerKN-2 represented by (8) in FIG. 3. The nucleotide sequence for the insertion fragment of KF14ΔEc was partially determined from the EcoRI site. Based on the nucleotide sequence obtained, primerKT5'Ec [5'AGCGGTCGACCTAATAAAGGAAAAGGGGAA3', (11) in FIG. 3] (SEQ ID NO: 11) was synthesized. Also, based on a part of the previously determined nucleotide sequence for the insertion fragment of pKF-Kpn11, primerKT3'Hd [5'GGAAGCTTTTTTGTAAAACAGA TTTTTTGCCCCGCTT3', (12) in FIG. 3] (SEQ ID NO: 12) was synthesized. Using these two primers and using 2 μg of DNA from the flocculent meiotic segregant strain KMS004 as a template, PCR was carried out with LA-PCR Kit. The reaction was conducted as follows: 1 cycle at 94° C. for 1 minutes followed by 30 cycles at 98° C. for 20 seconds and at 68° C. for 10 minutes. As a result of the electrophoresis of the reaction products using 0.8% agarose, it was observed that a DNA fragment of about 9 kb [(13) in FIG. 3] was amplified. Since this fragment contained the BamHI and XbaI sites indicated in the restriction map shown in FIG. 2, it was judged that the full length of Lg-FLO1 is contained in this fragment. Hereinafter, this PCR fragment is called the Lg-FLO1 full length fragment. The Lg-FLO1 full length fragment was digested with several restriction enzymes and the resultant digests were electrophoresed using 0.8% agarose gel. Then, the sizes of restriction fragments were determined and a restriction map was prepared. FIG. 4 shows a restriction map of the the Lg-FLO1 full length fragment.

(6) Introduction of the Lg-FLO1 Full Length Fragment into Yeast and Characterization of Flocculating Property As a host yeast strain for examination of phenotype changes due to the introduction of Lg-FLO1, KY644 strain was used which is an FLO1-disrupted strain prepared by the following procedures. Briefly, an FLO1 partial length fragment was ligated to pRS405 (Stratagene) between the BamHI and HindIII sites. This plasmid was cut at the sole BstEII site which exists only in the insertion fragment and then introduced into a flocculent yeast strain, KY642 (a, ura3, leu2, FLO8), by the lithium method, to thereby obtain a strain which has become non-flocculent due to homologous recombination at the FLO1 locus. It was confirmed by Southern analysis that the FLO1 gene of this strain had been disrupted by the introduction of pRS405. This strain was designated as KY644 strain.

The Lg-FLO1 full length fragment has been PCR-amplified with primers which had been so designed to give the fragment a SalI site at 5' end and a HindIII site at 3' end. This fragment was digested with SalI and HindIII. As a cloning vector, pYT37 was used which had been obtained by introducing into the EcoRI site of YIp5 the following two fragments: a fragment containing the nucleotide sequence for CEN3 obtained from Entrez (National Center for Biotechnology Information), a databank for DNA sequences, as well as a CEN3 of 1.2 kb obtained by PCR based on the whole nucleotide sequence for the yeast chromosome No. 3, and a fragment containing an ARS sequence obtained as a YRP7-derived EcoRI-HindIII fragment. The Lg-FLO1 full length fragment was ligated to pYT37 between the SalI and HindIII sites, and then introduced directly into KY644 strain by the lithium method.

DNA's from the resultant transformants were subjected to Southern analysis. As a result, it was confirmed that the Lg-FLO1 full length fragment was introduced in one strain. The plasmid contained in this strain (designated as KY650) was designated as KTYT2. With respect to KY650 strain and a strain (designated as KY652 strain) obtained by introducing only the vector pYT37 into KY650, characterization of flocculating property was carried out by the method as previously described after they were cultured until reaching stationary phase in the medium shown in Table 1 at 20° C. under shaking. In order to examine inhibition of flocculation by sugars, sugars were added to the flocculation measurement buffer at the final concentration of 1M. The results are shown in Table 2.

TABLE 2

Flocculating Property of
Lg-FL01 Full Length Fragment-Introduced Yeast Strain

| Strain | KY650 | KY652 (Control) |
|---|---|---|
| No sugar | + | − |
| Mannose | − | − |
| Glucose | − | − |
| Maltose | − | − |
| Galactose | + | − |
| Fructose | − | − |

"+" represents flocculent and
"−" non-flocculent.

While KY652 strain did not exhibit flocculating property under any of the conditions, KY650 strain containing the Lg-FLO1 full length fragment exhibited flocculating property in the flocculation measurement buffer when no sugar was added. This flocculating property was inhibited by mannose, glucose and maltose and somewhat inhibited by fructose, but was not inhibited by galactose. From these results, it was concluded that, by introducing the Lg-FLO1 full length fragment, it is possible to confer on laboratory yeast the brewer's yeast-type flocculating property.

[EXAMPLE 2]

Acquisition of the Coding Region of Lg-FLO1 by PCR, Introduction of the Same into Laboratory Yeast and Evaluation With respect to an adjacent region to the part ligated to the vector in the insertion fragment of KF14, the nucleotide sequence was determined by the method described above. As a result, a site which appeared to be the translation initiation site of Lg-FLO1 was found 49 bp upstream to 5' of the insertion fragment of KF1. PrimerKTF7 [5'CCCCAAGCTTGCTCTGCAGTAAATTCCGCA3', (14) in FIG. 3] (SEQ ID NO: 13) to be used for PCR from 58 bp upstream to 5' of this initiation codon in the direction toward 3' was synthesized. Also, based on the previously determined nucleotide sequence for the insertion fragment of pKF-Kpn11, primerKTORFA [5'CGGAATTCTAAACACTATAAGCGTGATGATAG3', (15) in FIG. 3] (SEQ ID NO: 14) to be used for PCR from 53 bp downstream to 3' of the termination codon of the Lg-FLO1 coding region in the direction toward 5' was synthesized. Using these two primers and using 2 μg of DNA from the flocculent meiotic segregant strain KMS004 as a template, PCR was carried out with LA-PCR Kit. The reaction was conducted by repeating 30 cycles of at 94° C. for 30 seconds, at 60° C. for 1 minute and at 72° C. for 3.5 minutes. As a result of electrophoresis of the reaction products using 0.8% agarose, it was observed that a DNA fragment of about 5.8 kb [(16) in FIG. 3] was amplified. Hereinafter, this PCR fragment is called the Lg-FLO1ORF fragment. The Lg-FLO1ORF fragment was PCR-amplified with primers which had been so designed to give the fragment a HindIII site at 5' end and a EcoRI site at 3' end. This fragment was digested with HindIII and EcoRI and ligated to the yeast expression vector pYES2 (Invitrogen) between the HindIII and EcoRI sites in such a manner that the fragment was inserted in the downstream of the GAL1 promoter in the sense direction. Then, the vector was directly introduced to the KY644 strain described above by the lithium method. DNA's from the resultant transformants were subjected to Southern analysis, and one of those strains in which the introduction of the Lg-FLO1ORF fragment had been confirmed was designated as KY646 strain. Also, the plasmid contained in KY646 strain was designated as YESKT2. With respect to KY646 strain and a strain (designated as KY649 strain) obtained by introducing only the vector pYES2 into KY644 strain, characterization of flocculating property was carried out by the method as previously described after they were cultured until reaching stationary phase in the medium shown in Table 1 at 20° C. under shaking. The results are shown in Table 3.

TABLE 3

Flocculating Property of Yeast Strain into which
GAL1 Promoter-Controlled Lg-FL01ORF Fragment is Introduced

| Strain | KY646 | KY649 (Control) |
|---|---|---|
| No sugar | + | − |
| Mannose | − | − |
| Glucose | − | − |
| Maltose | − | − |
| Galactose | + | − |
| Fructose | − | − |

"+" represents flocculent and
"−" non-flocculent.

While KY649 strain did not exhibit flocculating property under any of the conditions, KY646 strain containing the Lg-FLO1ORF fragment exhibited flocculating property in the flocculation measurement buffer when no sugar was added. This flocculating property was, similar to that of KY650 strain, the brewer's yeast-type flocculating property. In other words, this flocculating property was inhibited by mannose, glucose and maltose and somewhat inhibited by fructose, but was not inhibited by galactose. From these results, it was concluded that, by introducing the Lg-FLO1 ORF fragment controlled by GAL1 promoter, it is possible to confer on laboratory yeast the brewer's yeast-type flocculating property. In other words, it was concluded that the coding region of the Lg-FLO1 gene exists in the Lg-FLO1ORF fragment.

[EXAMPLE 3]

Figure 5:
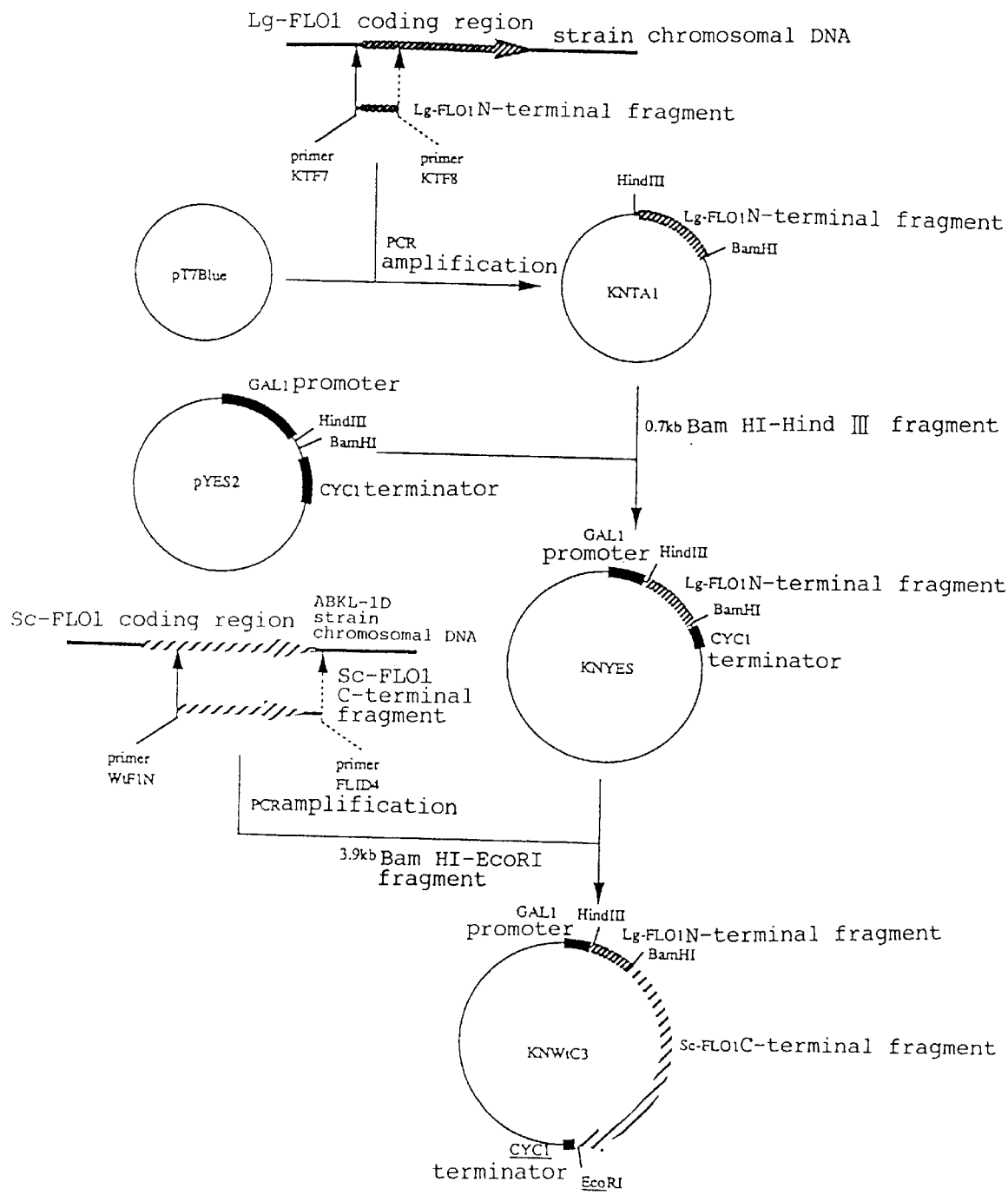
FIG. 5 is a concept diagram showing the construction of an Lg-Sc-chimeric FLO1 gene.

Specification of the Region in Lg-FLO1 Controlling Brewer's Yeast-Type Flocculation In order to specify the region in Lg-FLO1 which controls the brewer's yeast-type flocculation, a chimeric gene composed of Lg-FLO1 and Sc-FLO1 [laboratory yeast-type FLO1 disclosed by Watari et al., Yeast, 10, 211–225 (1994)] was created by the method as shown in FIG. 5 and investigated into the flocculating property thereof. The Lg-FLO1 ORF fragment was digested with XhoI and KpnI, bluntended with Klenow fragment and then cloned into the HincII site of pUC118. Of the resultant transformants, one clone having an insertion fragment of about 1 kb was selected and the nucleotide sequence for the insertion fragment was determined. Based on the result, primerKTF8 (5'CGGGATCCATCTGGCAATACCACACTAACA3') (SEQ ID NO: 15) was synthesized which extends from 639 bp downstream to 3' of the initiation codon of Lg-FLO1 toward 5'. Using primerKTF7 and primerKTF8 and using as a template 2 μg of DNA from the flocculent meiotic segregant strain KMS004, PCR was carried out with LA-PCR Kit. The reaction was conducted by repeating 30 cycles of at 94° C. for 30 seconds, at 60° C. for 1 minute and at 72° C. for 3.5 minutes. As a result of electrophoresis of the reaction products using 0.8% agarose, it was observed that a fragment of about 0.7 kb [(16) in FIG. 3] was amplified. Hereinafter, this PCR fragment is called the Lg-FLO1 N-terminal fragment. The fragment obtained was cloned into pT7Blue (Novagen) which is a cloning vector for PCR products. Using four independent clones obtained, the nucleotide sequences for their insertion fragments were determined from both directions. All of these four clones were found to have the same insertion fragment. The nucleotide sequence obtained is shown in SEQ ID NO: 1. One of these clones was designated as KNTA1. The Lg-FLO1 N-terminal fragment was PCR-amplified with primers which had been so designed to give the fragment a HindIII site at 5' end and a BamHI site at 3' end. KNTA1 was digested with HindIII and BamHI and subjected to electrophoresis. Then, the insertion fragment separated from the vector was cut out from the gel, purified by the method as described above and cloned into the HindIII-BamHI site of pYES2 in such a manner that the fragment was inserted in the downstream of the GAL1 promoter in the sense direction. The plasmid obtained was designated as KNYES. *Escherichia coli* EKB707 containing this plasmid KNYES was deposited at the National Institute of Bioscience and Human-Technology, Agency of Industrial Science and Technology (1–3, Higashi 1-Chome, Tsukuba City, Ibaragi Pref., Japan) on Jan. 27, 1995 under the accession No. FERM BP-4983.

Based on the nucleotide sequence for the laboratory yeast-type FLO1 gene (hereinafter referred to as the "Sc-FLO1 gene") which Watari et al. disclosed [Yeast, 10, 211–225 (1994)], primerWtF1N (5'CGGGATCCACTGTAAGTGATGACTTCGAAG3') (SEQ ID NO: 16) extending from 721 bp downstream to 3' of the initiation codon toward 3' and primerFLID4 (5'CGGAATTCTCAGCGTATAATTAGCAAAGAA3') (SEQ ID NO: 17) extending from 58 bp downstream to 3' of the termination codon toward 5' were synthesized. Using these primers and using as a template 2 μg of DNA from ABXL-1D strain, PCR was carried out with LA-PCR Kit. The reaction was conducted by repeating 30 cycles of at 94° C. for 30 seconds, at 60° C. for 1 minute and at 72° C. for 3.5 minutes. As a result of electrophoresis of the reaction products using 0.8% agarose, it was observed that a fragment of about 3.9 kb was amplified. Hereinafter, this fragment is called the Sc-FLO1 C-terminal fragment. The Sc-FLO1 C-terminal fragment was PCR-amplified with primers which had been so designed to give the fragment a BamHI site at 5' end and an EcoRI site at 3' end. This fragment was digested with BamHI and EcoRI, and ligated to the previously constructed KNYES between BamHI and EcoRI sites in such a manner that the fragment was inserted in the downstream of the Lg-FLO1 N-terminal fragment in the sense direction. As a result, it is expected that a gene coding for a chimeric FLO1 protein is constructed in which a portion of the Sc-FLO1 coding region corresponding to the amino acid sequence from the amino terminal to position 339 has been replaced with a portion of the Lg-FLO1 gene corresponding to the amino acid sequence from the amino terminal to position 312. The ligation reaction product was introduced directly to the KY644 strain described above by the lithium method. DNA's from the resultant transformants were subjected to Southern analysis. Of those strains in which the introduction of the chimeric gene composed of the Lg-FLO1 N-terminal fragment and the Sc-FLO1 C-terminal fragment was confirmed, one strain was designated as KY648 strain. Also, the plasmid contained in this strain was designated as KNWtC3.

Further, primerFLID1 (5'CCCCAAGCTTTCGTTT GATGTAAGCTCTCT3') (SEQ ID NO: 18) which is extending from −69 bp upstream to 5' of the initiation codon of Sc-FLO1 toward 3' was synthesized. Using primerFLID1 and primerFLID4 and using as a template 2 μg of DNA from ABXL-1D strain, PCR was carried out with LA-PCR Kit. The reaction was conducted by repeating 30 cycles of at 94° C. for 30 seconds, at 60° C. for 1 minute and at 72° C. for 3.5 minutes. As a result of electrophoresis of the reaction products using 0.8% agarose, it was observed that a fragment of about 4.8 kb was amplified. Hereinafter, this fragment is called the Sc-FLO1ORF fragment. The Sc-FLO1ORF fragment was PCR-amplified with primers which had been so designed to give the fragment a HindIII site at 5' end and an EcoRI site at 3' end. This fragment was digested with HindIII and EcoRI, and ligated to pYES2 between the HindIII and EcoRI sites in such a manner that the fragment was inserted in the downstream of GAL1 promoter in the sense direction. The resultant vector was introduced directly to the above-mentioned KY644 strain by the lithium method. DNA's from the resultant transformants were subjected to Southern analysis. Of those strains in which the introduction of the Sc-FLO1ORF fragment was confirmed, one strain was designated as KY647 strain and used for the comparison of flocculating properties. Also, the plasmid contained in this strain was designated as YESWt1.

With respect to KY647 strain, KY648 strain and the previously described KY649 strain, characterization of flocculating property was carried out by the method as previously described after they were cultured until reaching stationary phase in the medium shown in Table 1 at 20° C. under shaking. The results are shown in Table 4.

TABLE 4

| Flocculating Property of Yeast Strain into which GAL1 Promoter-Controlled Lg-Sc Chimeric FL01 Gene is Introduced | | | |
|---|---|---|---|
| Strain | KY648 | KY649 (Control) | KY647 (Comparison) |
| No sugar | + | − | + |
| Mannose | − | − | − |
| Glucose | − | − | + |
| Maltose | − | − | + |
| Galactose | + | − | + |
| Fructose | − | − | + |

"+" represents flocculent and
"−" non-flocculent.

While KY649 strain did not exhibit flocculating property under any of the conditions, KY648 strain containing the chimeric gene composed of the Lg-FLO1 N-terminal fragment and the Sc-FLO1 C-terminal fragment and KY647 strain containing the Sc-FLO1ORF fragment exhibited flocculating property in the flocculation measurement buffer when no sugar was added. The flocculating property of KY648 was, similar to that of KY650, inhibited by mannose, glucose and maltose and somewhat inhibited by fructose, but was not inhibited by galactose. On the other hand, the flocculating property of KY647 was only inhibited by mannose, but was not inhibited by glucose, maltose, fructose nor galactose. In other words, while the Sc-FLO1ORF fragment confers laboratory yeast-type flocculating property, the flocculating property conferred by the chimeric gene prepared by replacing a portion of this fragment extending from its initiation codon to 720 bp toward 3' with a portion of Lg-FLO1 extending from the initiation codon to 639 bp toward 3' was converted to the brewer's yeast-type. From these results, it was concluded that what is deeply involved in the conferring of brewer's yeast-type flocculating property is the Lg-FLO1 N-terminal fragment in the Lg-FLO1ORF fragment, i.e., the sequence shown in SEQ ID NO: 1 of the Sequence Listing.

[EXAMPLE 4]

Evaluation of Lg-FLO1-Disrupted Brewer's Yeast
(1) Preparation of a Plasmid for Disrupting Lg-FLO1

Figure 6:
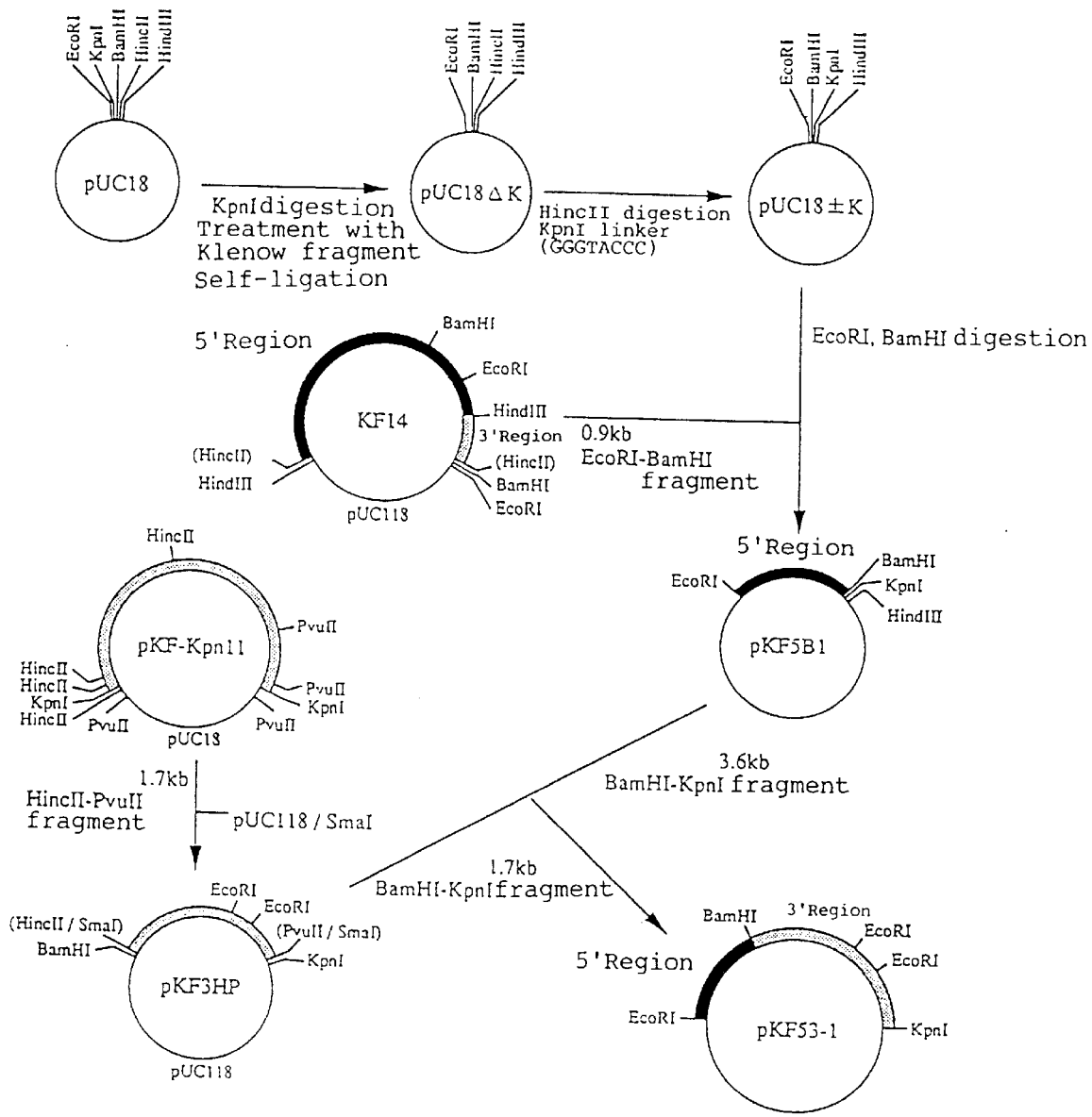
FIG. 6 is a chart showing the construction of a plasmid for destroying the Lg-FLO1 gene.
Figure 7:
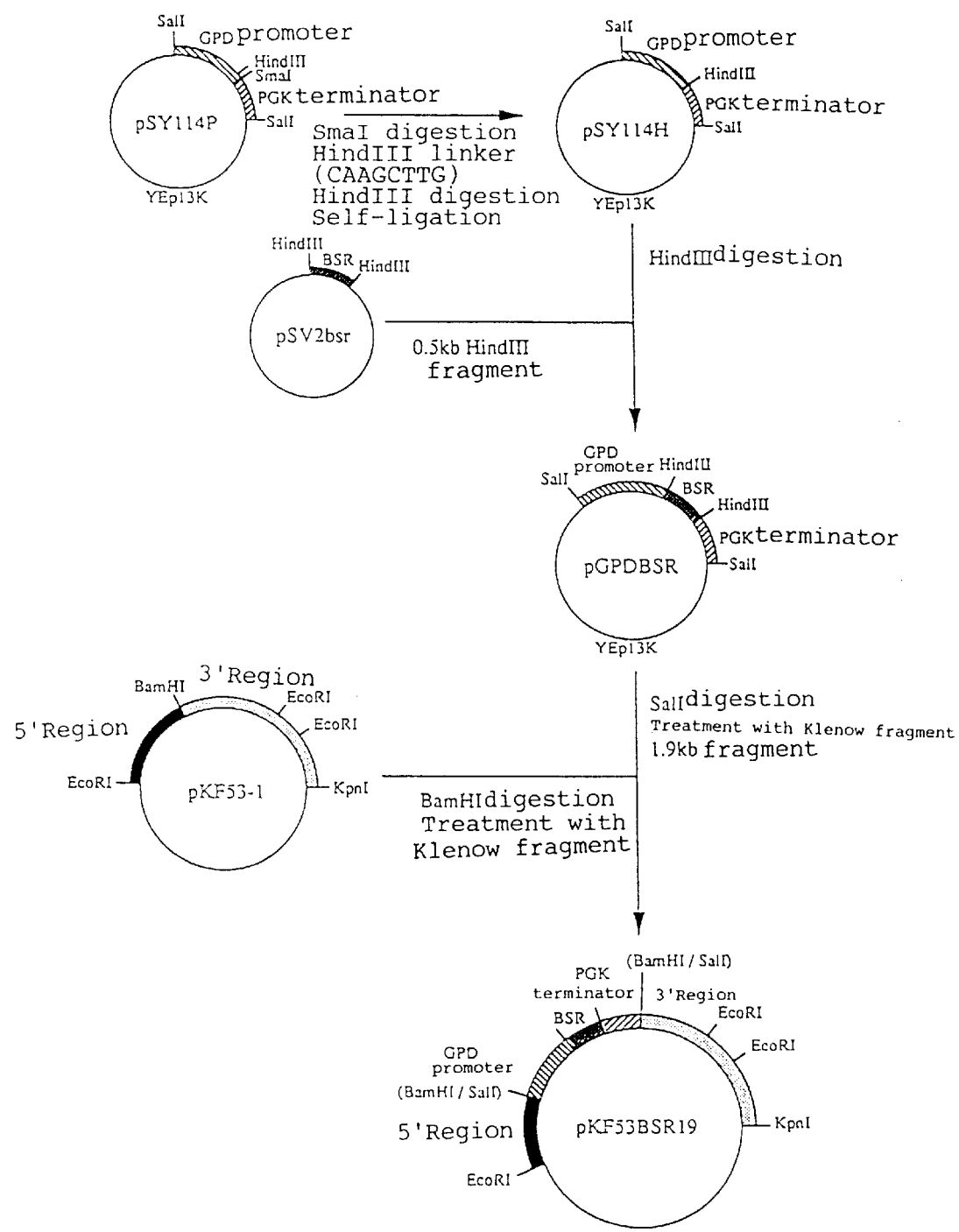
FIG. 7 is a chart (continued) showing the construction of a plasmid for disrupting the Lg-FLO1 gene.

A Plasmid for disrupting Lg-FLO1 was prepared as shown in FIGS. 6 and 7. Briefly, plasmid pUC18 was digested with KpnI and then DNA fragments blunt-ended with Klenow fragment were self-ligated, to thereby prepare plasmid pUC18ΔK. This plasmid was digested with HincII and then a KpnI linker (GGGTACCC) was inserted thereinto, to thereby prepare plasmid pUC18±K. Between the EcoRI and BamHI sites of this plasmid, a 0.9 kb EcoRI-BamHI fragment (containing 5' flanking region) obtained from plasmid KF14 was inserted to thereby prepare plasmid pKF5B1.

From plasmid pKF3HP which was obtained by inserting a 1.7 kb HincII-PvuII fragment (containing 3' flanking region) into the SmaI site of plasmid pUC118, a 1.7 kb BamHI-KpnI fragment was obtained and inserted between the BamHI and KpnI sites of plasmid pKF5B1, to thereby prepare plasmid pKF53-1.

Plasmid pSY114P (Japanese Unexamined Patent Publication No. 2-265488) which contains a promoter region (1.0 kb) from yeast GPD (glyceraldehyde-3-phosphate dehydrogenase) gene and a terminator region (0.4 kb) from yeast PGK (phosphoglycerate kinase) gene was digested with SmaI and then a HindIII linker (CAAGCTTG) was ligated thereto. Subsequently, the plasmid was digested with HindIII and then self-ligated, to thereby prepare plasmid pSY114H. To the HindIII site of this plasmid, a 0.5 kb HindIII fragment of pSV2bsr (Funakoshi) containing a Blasticidin S resistant gene was inserted to thereby prepare plasmid pGPDBSR. This plasmid was digested with SalI and then blunt-ended with Klenow fragment, to thereby obtain a 1.9 kb DNA fragment. This DNA fragment was ligated to a DNA fragment obtained by digesting plasmid pKF53-1 with BamHI and then blunt-ending with Klenow fragment, to thereby prepare plasmid pKF53BSR19.

(2) Transformation of Brewer's Yeast

Transformation of brewer's yeast was performed by electroporation. Flocculent brewer's yeast cultured in 200 ml of YPD medium until OD600 reached approximately 7 was washed twice with sterilized water and twice with 1M sorbitol, and then resuspended in 1 ml of 1M sorbitol. To 50 μl of this yeast suspension, 2.7 μg of DNA fragments obtained by digesting plasmid pKF53BSR with EcoRI and 10 μg of salmon sperm (DNA) (Sigma) were added and left for 5 minutes. Then, using a 0.2 cm cell of the Gene Pulser (Bio Rad), an electric pulse of 1.5 KV, 25 μF and 200Ω was charged. To the resultant suspension, 1 ml of 1M sorbitol and 400 μl of YPD were added and cultured at 30° C. for 4 hours under shaking. Thereafter, the suspension was plated on YPD agar medium containing 50 μg/ml Blasticidin S (Funakoshi) and cultured at 30 ° C. for 3 days. The resultant transformants were subjected to Southern analysis and, as a result, it was confirmed that the Lg-FLO1 gene was disrupted. The thus obtained Lg-FLO1-disrupted brewer's yeast was evaluated for flocculating property and was found to have been converted to non-flocculent.

[EXAMPLE 5]

Comparison of the Deduced Amino Acid Sequences of the N-Terminal Region for Lg-FLO1 and SC-FLO1

Example 3 has shown that brewer's yeast-type flocculating property is controlled by the sequence of 213 amino acid residues in the N-terminal region of Lg-FLO1. Then, the deduced amino acid sequences of this region for Lg-FLO1 and Sc-FLO1 were compared. As a result, as shown in FIG. 8, the following characteristic differences were observed between the two sequences. 1) In Lg-FLO1, 27 amino acid residues corresponding to those from position 84 to position 110 of Sc-FLO1 are deleted. 2) Up to the position 123 based on Sc-FLO1, homology between Sc-FLO1 and Lg-FLO1 is relatively low. 3) At the position 124 and thereafter based on Sc-FLO1, homology between Sc-FLO1 and Lg-FLO1 is high.

Based on these results, there were prepared a chimeric gene composed of Sc-FLO1 and Lg-FLO1 and a modified Sc-FLO1 gene having a deletion of the 27 amino acid residues from position 84 to position 110. The N-terminal regions of these modified FLO1 genes were prepared using the recombinant PCR method described on pages 155–160 of PCR Experiment Manual [M. A. Innis et al. (eds.), edited and translated by Takashi Saito, HBJ Shuppan Co., Ltd. (1991)]. A fragment of the thus prepared T-terminal region of the modified FLO1 gene was ligated to plasmid KNWtC3 (described in Example 3) between the HindIII and BamHI sites (i.e., between GAL1 promoter and the Sc-FLO1 C-terminal fragment) in the sense direction, and then introduced into the yeast KY644 strain. Culture of the resultant transformants and evaluation of flocculating property were carried out in substantially the same manner as in Example 3. The results are shown in FIG. 9. Those strains (KY707, KY708 and KY709) having a chimeric FLO1 gene composed of an Lg-FLO1-derived portion up to amino acid residue at position 46, 68 or 83 (based on Sc-FLO1) and an Sc-FLO1-derived portion following the above portion exhibited, similar to a strain having Sc-FLO1 (KY706), strong laboratory yeast-type flocculation. On the other hand, a strain having a chimeric FLO1 gene composed of an Lg-FLO1-derived portion up to amino acid residue at position 124 based on Sc-FLO1 (position 97 based on Lg-FLO1) and an Sc-FLO1-derived portion following the above portion exhibited, similar to KY648 and KY646 shown in Example 3, weak brewer's yeast-type flocculation. Further, KY711 having a modified FLO1 gene having a deletion of the 27 amino acid residues from position 84 to position 110 of Sc-FLO1 exhibited weak laboratory yeast-type flocculation. From these results, it has been shown that the portion of the Lg-FLO1 gene involved in brewer's yeast-type is a portion corresponding to the 14 amino acid residues from position 84 to position 97 based on Lg-FLO1, i.e., the sequence shown in SEQ ID NO: 3 coding for the amino acid sequence shown in SEQ ID NO: 4 in the Sequence Listing.

Industrial Applicability

According to the present invention, there are provided the Lg-Flo1 protein having an activity to confer on yeast brewer's yeast-type flocculating property as well as the Lg-FLO1 DNA strand coding for the protein. By introducing the DNA of the invention into yeast as a foreign DNA, i.e., introducing this DNA into yeast cells as an extranuclear gene and(/or) a nuclear gene, it is possible to confer on yeast brewer's yeast-type flocculating property or enhance the property in yeast. On the contrary, by introducing a DNA obtained by disrupting the DNA of the invention into yeast cells, or by inhibiting the expression of the DNA of the invention, it is possible to convert a flocculent yeast strain into a non-flocculent yeast strain, or to reduce flocculating property.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 697 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 59..697

( x i ) SEQUENCE DESCRIPTION: SEQ ID NO:1:

```
GCTCTGCAGT AAATTCCGCA AATGATTTTC TTTAAATTGA TTAGCACCAC TAAAAAAA                      58

ATG ACA ATT GCA CAC CAC TGC ATA TTT TTG GTA ATC TTG GCC TTT CTG                     106
Met Thr Ile Ala His His Cys Ile Phe Leu Val Ile Leu Ala Phe Leu
 1               5                  10                  15

GAG CTA CTT AAC GTA GCA TCA GGA AGT ACA CAA GCA TGC CTG CCA GTG                     154
Glu Leu Leu Asn Val Ala Ser Gly Ser Thr Gln Ala Cys Leu Pro Val
             20                  25                  30

GGC TCG AGG AAA AAT GGG ATG AAT GTC AAC TTT TAT AAA TAC TCA TTA                     202
Gly Ser Arg Lys Asn Gly Met Asn Val Asn Phe Tyr Lys Tyr Ser Leu
         35                  40                  45

CAG GAT TCA ACA ACG TAT TCC GAC CCG CAA TAT ATG GCC TAT AAA TAC                     250
Gln Asp Ser Thr Thr Tyr Ser Asp Pro Gln Tyr Met Ala Tyr Lys Tyr
     50                  55                  60

TCC GAT ACA AAG AAG TTA GGT TCC GTT AGC GGA CAG ACC CAT CTC TCC                     298
Ser Asp Thr Lys Lys Leu Gly Ser Val Ser Gly Gln Thr His Leu Ser
 65                  70                  75                  80

ATA TAC TAT GGC CCA AAT ACT GCC TTT TGG AAT ACT GCC TCT TGG AGT                     346
Ile Tyr Tyr Gly Pro Asn Thr Ala Phe Trp Asn Thr Ala Ser Trp Ser
                 85                  90                  95

TCT GAT CTT TTT GGT TTC TAT ACT ACT CCA ACT AAT GTA ACT GTG GAA                     394
Ser Asp Leu Phe Gly Phe Tyr Thr Thr Pro Thr Asn Val Thr Val Glu
            100                 105                 110

ATG ACA GGG TAC TTT TTA CCA CCA CAG ACG GGT TCT TAC ACA TTC AAG                     442
Met Thr Gly Tyr Phe Leu Pro Pro Gln Thr Gly Ser Tyr Thr Phe Lys
        115                 120                 125

TTT GCT ACA GTT GAC GAC TCT GCA ATT TTA TCG GTT GGT GGT AGC ATT                     490
Phe Ala Thr Val Asp Asp Ser Ala Ile Leu Ser Val Gly Gly Ser Ile
    130                 135                 140

GCG TTC GAA TGT TGT GCA CAA GAA CAA CCT CCT ATC ACA TCA ACG GAT                     538
Ala Phe Glu Cys Cys Ala Gln Glu Gln Pro Pro Ile Thr Ser Thr Asp
145                 150                 155                 160

TTC ACT ATT AAC GGT ATT AAA CCA TGG GAC GCA GCT GCA CCT ACC GAC                     586
Phe Thr Ile Asn Gly Ile Lys Pro Trp Asp Ala Ala Ala Pro Thr Asp
                165                 170                 175

ATA AAG GGG TCA ACG TAC ATG TAC GCC GGT TAC TAT TAC CCG ATC AAA                     634
Ile Lys Gly Ser Thr Tyr Met Tyr Ala Gly Tyr Tyr Tyr Pro Ile Lys
            180                 185                 190

ATT GTT TAT TCA AAT GCT AAA GTC TTG GCT AGG CTT CCT GTT AGT GTG                     682
Ile Val Tyr Ser Asn Ala Lys Val Leu Ala Arg Leu Pro Val Ser Val
        195                 200                 205

GTA TTG CCA GAT GGA                                                                 697
Val Leu Pro Asp Gly
    210
```

( 2 ) INFORMATION FOR SEQ ID NO:2:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Ile  Ala  His  His  Cys  Ile  Phe  Leu  Val  Ile  Leu  Ala  Phe  Leu
 1              5                        10                       15

Glu  Leu  Leu  Asn  Val  Ala  Ser  Gly  Ser  Thr  Gln  Ala  Cys  Leu  Pro  Val
               20                       25                       30

Gly  Ser  Arg  Lys  Asn  Gly  Met  Asn  Val  Asn  Phe  Tyr  Lys  Tyr  Ser  Leu
          35                       40                       45

Gln  Asp  Ser  Thr  Thr  Tyr  Ser  Asp  Pro  Gln  Tyr  Met  Ala  Tyr  Lys  Tyr
     50                        55                       60

Ser  Asp  Thr  Lys  Lys  Leu  Gly  Ser  Val  Ser  Gly  Gln  Thr  His  Leu  Ser
 65                      70                       75                       80

Ile  Tyr  Tyr  Gly  Pro  Asn  Thr  Ala  Phe  Trp  Asn  Thr  Ala  Ser  Trp  Ser
               85                       90                       95

Ser  Asp  Leu  Phe  Gly  Phe  Tyr  Thr  Thr  Pro  Thr  Asn  Val  Thr  Val  Glu
               100                      105                      110

Met  Thr  Gly  Tyr  Phe  Leu  Pro  Pro  Gln  Thr  Gly  Ser  Tyr  Thr  Phe  Lys
          115                      120                      125

Phe  Ala  Thr  Val  Asp  Asp  Ser  Ala  Ile  Leu  Ser  Val  Gly  Gly  Ser  Ile
     130                      135                      140

Ala  Phe  Glu  Cys  Cys  Ala  Gln  Glu  Gln  Pro  Pro  Ile  Thr  Ser  Thr  Asp
145                      150                      155                      160

Phe  Thr  Ile  Asn  Gly  Ile  Lys  Pro  Trp  Asp  Ala  Ala  Ala  Pro  Thr  Asp
               165                      170                      175

Ile  Lys  Gly  Ser  Thr  Tyr  Met  Tyr  Ala  Gly  Tyr  Tyr  Tyr  Pro  Ile  Lys
               180                      185                      190

Ile  Val  Tyr  Ser  Asn  Ala  Lys  Val  Leu  Ala  Arg  Leu  Pro  Val  Ser  Val
          195                      200                      205

Val  Leu  Pro  Asp  Gly
          210
```

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..42

( i x ) FEATURE:
        ( A ) NAME/KEY: mat_peptide
        ( B ) LOCATION: 1..42

( x i ) SEQUENCE DESCRIPTION: SEQ ID NO:3:

```
GGC  CCA  AAT  ACT  GCC  TTT  TGG  AAT  ACT  GCC  TCT  TGG  AGT  TCT         42
Gly  Pro  Asn  Thr  Ala  Phe  Trp  Asn  Thr  Ala  Ser  Trp  Ser  Ser
 1              5                        10
```

( 2 ) INFORMATION FOR SEQ ID NO:4:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

Gly Pro Asn Thr Ala Phe Trp Asn Thr Ala Ser Trp Ser Ser
1               5                   1 0

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Xaa Thr Gln Ala Cys Leu Pro Val Gly Xaa Arg Lys Asn Gly Met Asn
1               5                   1 0                  1 5

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATGAAACTG TCATTGTTGT CAAA                                    2 4

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TCGTTTCAGC AGCTAAAGTA T                                       2 1

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AATACACAAC ATGGTGTCCT                                         2 0

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ACCAGAGGTG GAACTACTGG                                         2 0

( 2 ) INFORMATION FOR SEQ ID NO:10:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

TTGTATCGGA GTATTTATA 19

( 2 ) INFORMATION FOR SEQ ID NO:11:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

AGCGGTCGAC CTAATAAAGG AAAAGGGGAA 30

( 2 ) INFORMATION FOR SEQ ID NO:12:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GGAAGCTTTT TTGTAAAACA GATTTTTGC CCCGCTT 37

( 2 ) INFORMATION FOR SEQ ID NO:13:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

CCCCAAGCTT GCTCTGCAGT AAATTCCGCA 30

( 2 ) INFORMATION FOR SEQ ID NO:14:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

CGGAATTCTA AACACTATAA GCGTGATGAT AG 32

( 2 ) INFORMATION FOR SEQ ID NO:15:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

CGGGATCCAT CTGGCAATAC CACACTAACA 30

( 2 ) INFORMATION FOR SEQ ID NO:16:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:16:

CGGGATCCAC TGTAAGTGAT GACTTCGAAG 30

(2) INFORMATION FOR SEQ ID NO:17:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:17:

CGGAATTCTC AGCGTATAAT TAGCAAAGAA 30

(2) INFORMATION FOR SEQ ID NO:18:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:18:

CCCCAAGCTT TCGTTTGATG TAAGCTCTCT 30

(2) INFORMATION FOR SEQ ID NO:19:

(i) SEQUENCE CHARACTERISTICS:
(A) LENGTH: 240 amino acids
(B) TYPE: amino acid
(C) STRANDEDNESS: single
(D) TOPOLOGY: linear (xi) SEQUENCE DESCRIPTION: SEQ ID NO:19:

```
Met Thr Met Pro His Arg Tyr Met Phe Leu Ala Val Phe Thr Leu Leu
 1               5                  10                  15

Ala Leu Thr Ser Val Ala Ser Gly Ala Thr Glu Ala Cys Leu Pro Ala
             20                  25                  30

Gly Gln Arg Lys Ser Gly Met Asn Ile Asn Phe Tyr Gln Tyr Ser Leu
             35                  40                  45

Lys Asp Ser Ser Thr Tyr Ser Asn Ala Ala Tyr Met Ala Tyr Gly Tyr
     50                  55                  60

Ala Ser Lys Thr Lys Leu Gly Ser Val Gly Gly Gln Thr Asp Ile Ser
65                   70                  75                  80

Ile Asp Tyr Asn Ile Pro Cys Val Ser Ser Ser Gly Thr Phe Pro Cys
                 85                  90                  95

Pro Gln Glu Asp Ser Tyr Gly Asn Trp Gly Cys Lys Gly Met Gly Ala
                100                 105                 110

Cys Ser Asn Ser Gln Gly Ile Ala Tyr Trp Ser Thr Asp Leu Phe Gly
            115                 120                 125

Phe Tyr Thr Thr Pro Thr Asn Val Thr Leu Glu Met Thr Gly Tyr Phe
        130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
                165                 170                 175

Ala Gln Gln Gln Pro Pro Ile Thr Ser Thr Asn Phe Thr Ile Asp Gly
```

-continued

|  |  |  |  |  |  |  |  |  |  |  |  |  |  |  |
|---|---|---|---|---|---|---|---|---|---|---|---|---|---|---|
|  |  |  | 180 |  |  |  |  | 185 |  |  |  | 190 |  |  |
| Ile | Lys | Pro<br>195 | Trp | Gly | Gly | Ser | Leu<br>200 | Pro | Pro | Asn | Ile | Glu<br>205 | Gly | Thr | Val |
| Tyr | Met<br>210 | Tyr | Ala | Gly | Tyr | Tyr<br>215 | Tyr | Pro | Met | Lys | Val<br>220 | Val | Tyr | Ser | Asn |
| Ala<br>225 | Val | Ser | Trp | Gly | Thr<br>230 | Leu | Pro | Ile | Ser | Val<br>235 | Thr | Leu | Pro | Asp | Gly<br>240 |

What is claimed is:

1. An isolated protein which comprises an amino acid sequence shown in SEQ ID NO: 2.

2. An isolated protein which comprises an amino acid sequence from position 25 to position 213 shown in SEQ ID NO: 2.

3. An isolated protein which comprises an amino acid sequence from position 25 to position 97 shown in SEQ ID NO: 2.

4. An isolated polypeptide which has an activity of conferring on yeast a flocculating property which is inhibited by each of maltose, glucose, and mannose and which comprises an amino acid sequence shown in SEQ ID NO: 4.

5. An isolated DNA comprising a nucleotide sequence coding for a protein according to claim 1.

6. An isolated DNA comprising a nucleotide sequence coding for a protein according to claim 2.

7. An isolated DNA comprising a nucleotide sequence coding for a protein according to claim 3.

8. An isolated DNA which comprises a partial sequence of the nucleotide sequence shown in SEQ ID NO: 1 containing the bases from position 59 to 697 or a DNA complementary thereto.

9. An isolated DNA according to claim 8 which comprises a partial sequence of the nucleotide sequence shown in SEQ ID NO: 1 containing the bases from position 131 to position 697 or a DNA complementary thereto.

10. An isolated DNA comprising a partial sequence of the nucleotide sequence shown in SEQ ID NO: 1 containing the bases from position 131 to position 349 or a DNA complementary thereto.

11. An isolated DNA which comprises the nucleotide sequence shown in SEQ ID NO; 3 and which codes for a polypeptide having an activity of conferring on yeast a flocculating property which is inhibited by each of maltose, glucose, and mannose, or an isolated DNA complementary thereto.

12. An isolated DNA comprising a nucleotide sequence that codes for a polypeptide according to claim 4.

13. A plasmid which is selected from the group consisting of KTYT2, YESKT2, KNYES, and KNWtC3.

14. A plasmid comprising the isolated DNA according to any one of claims 5 through 11 and 12.

15. A method for producing a yeast strain wherein a flocculating property which is inhibited by each of maltose, glucose, and mannose has been conferred or enhanced, comprising the steps of providing the isolated DNA according to any one of claims 5 through 11 and 12 and introducing said DNA into said yeast strain.

16. A method for producing a yeast strain wherein brewer's yeast-type flocculating property has been eliminated or reduced, comprising the steps of providing an isolated DNA of which the ability to express a protein having an activity of conferring a flocculating property which is inhibited by each of maltose, glucose, and mannose has been eliminated or reduced by disrupting the isolated DNA according to any one of claims 5 through 11 and 12 and introducing said DNA into said yeast strain.

17. A method for eliminating or reducing brewer's yeast-type flocculating property in yeast comprising:
   decreasing the ability of the isolated DNA according to any one of claims 5 through 11 and 12 to express the protein encoded by said isolated DNA by disrupting said isolated DNA to provide disrupted isolated DNA, and
   transforming said disrupted isolated DNA into a yeast strain, wherein brewer's yeast-type flocculating property in the transformed yeast strain is reduced or eliminated.

18. A yeast strain which is produced by the method according to claim 15.

19. A method for producing a brewed product comprising culturing the yeast strain according to claim 18.

20. A yeast strain which is produced by the method according to claim 16.

21. A method for producing a brewed product comprising culturing the yeast strain according to claim 20.

* * * * *